United States Patent
Ushio et al.

(10) Patent No.: US 6,348,617 B1
(45) Date of Patent: Feb. 19, 2002

(54) METHOD FOR PURIFYING PYRUVIC ACID COMPOUNDS

(75) Inventors: Hideki Ushio, Takatsuki; Motoo Hazama, Mishima-gun; Toshikazu Yagi, Nara; Akihiko Nakamura, Takatsuki; Masahiko Mizuno, Suita, all of (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/284,263

(22) PCT Filed: Oct. 8, 1997

(86) PCT No.: PCT/JP97/03595

§ 371 Date: Jun. 21, 1999

§ 102(e) Date: Jun. 21, 1999

(87) PCT Pub. No.: WO98/15520

PCT Pub. Date: Apr. 16, 1998

(30) Foreign Application Priority Data

Oct. 9, 1996 (JP) .............................. 8-268476
Apr. 3, 1997 (JP) .............................. 9-085211

(51) Int. Cl.⁷ .............................................. C09C 69/66
(52) U.S. Cl. ........................................ 560/174; 560/168
(58) Field of Search ................................. 560/168, 174

(56) References Cited

U.S. PATENT DOCUMENTS

| | | | |
|---|---|---|---|
| 4,399,287 A | | 8/1983 | Baillie et al. |
| 4,539,208 A | | 9/1985 | Kahan et al. |
| 4,616,038 A | | 10/1986 | Kahan et al. |
| 5,202,467 A | * | 4/1993 | Ikeda et al. .................. 560/174 |
| 5,268,501 A | | 12/1993 | Ikeda et al. |

FOREIGN PATENT DOCUMENTS

| | | |
|---|---|---|
| EP | 0387058 | 9/1990 |
| JP | 5661328 A | 5/1981 |
| JP | 59225144 A | 12/1984 |
| JP | 334938 | 2/1991 |
| JP | 334948 A | 2/1991 |
| JP | 4-210941 | 8/1992 |
| JP | 920723 A | 1/1997 |

OTHER PUBLICATIONS

Omote, Yoshimori et al., "Synthesis of 3–Alkyl–N–hydroxyindole–2–carboxylic Acid" Bull. Chem. Soc. Jpn., 1967, vol. 40, pp. 2703–2704.

"Aliphatic Compounds II (in Japanese)" Comprehensive Organic Chemistry, vol. 3, supervised by Mujio Kotake, Asakura Shten, Kozo Asakura, 1957, pp. 56, 57, 69.

R. L. Shriner et al., The Structure of the Bisulfite Compound of Acetaldehyde, J. Org. Chem., 6, 888 (1941).

Eric Montflier et al., "Double vs. mono carbonylation of phenethyl bromide catalyzed by cobalt complexes: effect of hydrophobic or water–soluble phosphines on the rate and selectivity of the reaction", J. Molecular Catalysis, 88 (1994) pp. 295–300.

Yoshimori Omote et al., Synthesis of 3–Alkyl–N–hydroxyindole–2–carboxylic Acid, Bulletin Chem., Soc. Japan 40, pp. 2703–2704 (1967).

Donald W. Graham et al., "Inhibition of the Mammalian –Lactamase Renal Dipeptidase (Dehydropeptidase–I) by (Z)–2–(Acylamino)–3–substituted–propenoic Acids", J. Med. Chem. 1987, 30, pp. 1074–1090.

Leonard M. Weinstock et al., "A General, One–Step Synthesis of α–Keto Esters", Synthetic Communication, 11(12), pp. 943–946 (1981).

Dai–Yukikagaku (Text on Organic Chemistry), Aliphatic Aldehyde, pp. 56–57 with its partial English translation.

Yukimasa Mitsuhashi et al., "Preparation and Characterization of Sulfite Adducts", Jpn. J. Toxicol. Environ. Health, 41(6), pp. 440–446 (1995).

March, Jerry. "Advanced Organic Chemistry", fourth edition, 1992, p. 895, paragraphs 6–12.

* cited by examiner

Primary Examiner—James O. Wilson
Assistant Examiner—Taylor V. Oh
(74) Attorney, Agent, or Firm—Birch, Stewart, Kolasch & Birch, LLP.

(57) ABSTRACT

The present invention is directed to a method for purifying pyruvic acid compounds, which method comprises reacting a pyruvic acid compound of general formula (I):

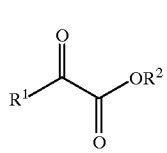

(I)

wherein R¹ is an optionally substituted lower alkyl group, a lower alkenyl group, a lower alkynyl group, a cycloalkyl group, an aryl group, or a heterocyclic group, and R² is a lower alkyl group, with a bisulfite of general formula (II):

MHSO₃ (II)

wherein M is NH₄ or an alkali metal, to give a bisulfite adduct of the pyruvic acid compound and then decomposing the adduct with an acid. According to the present invention, pyruvic acid compounds can be purified by simple and easy procedures without using purification techniques such as distillation or column chromatography, and the above method is advantageous as a process for the production on an industrial scale.

5 Claims, No Drawings

METHOD FOR PURIFYING PYRUVIC ACID COMPOUNDS

This application is the national phase under 35 U.S.C. §371 of PCT International Application No. PCT/JP97/03595 which has an International filing date of Oct. 8, 1997 which designated the United States of America.

1. Technical Field

The present invention relates to a method for purifying pyruvic acid compounds.

2. Background Art

Pyruvic acid compounds are useful as intermediates for the synthesis of drugs or amino acids, and as disclosed in JP-A 55-81845, for example, they have been used as intermediates for the production of antihypertensives. Ethyl 7-halo-2-oxoheptanoate, which is also a pyruvic acid compound, is an important intermediate of cilastatin. For the production thereof, there has been known a process in which an organic magnesium compound is reacted with diethyl oxalate according to the following scheme 1 (see JP-A 58-77885).

Scheme 1

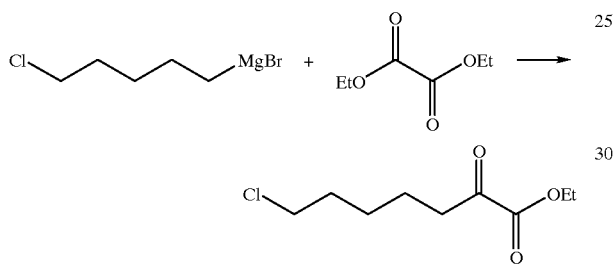

There has been known another process, for example, according to the following scheme 2, in which the synthesis is achieved by the reaction of a halide with ethyl 1,3-dithian-2-carboxylate and the subsequent deprotection [see J. Med. Chem., 30, 1074(1987)].

Scheme 2

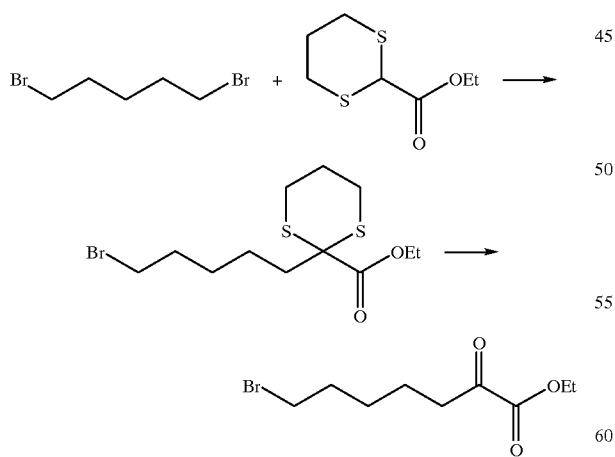

However, as described in the above references, the process according to scheme 1 has a defect in that the use of diethyl oxalate in excess makes the resulting pyruvic acid compound contaminated with diethyl oxalate and the process according to scheme 2 has a defect in that the use of a halide in excess and a base such as sodium hydride in mineral oil makes the resulting pyruvic acid compound contaminated with the halide and the mineral oil. Therefore, for obtaining pyruvic acid compounds, it requires the purification of intermediates or final pyruvic acid compounds by rectification or column chromatography.

For this reason, there has been sought a simple and easy method for purification by which the respective intermediates for synthesis or pyruvic acid compounds with high purity can be obtained without subjecting to a technique such as distillation or column chromatography.

Under these circumstances, the present inventors have intensively studied to develop a method in which pyruvic acid compounds can be purified by simple and easy procedures without using distillation, chromatography or any other techniques. As a result, they have found that the purification of a pyruvic acid compound can be achieved with high purity in a simple and easy manner by reacting the pyruvic acid compound with a bisulfite to give a bisulfite adduct of the pyruvic acid compound and then decomposing the adduct with an acid, thereby completing the present invention.

DISCLOSURE OF THE INVENTION

The present invention thus provides a method for purifying a pyruvic acid compound of general formula (I):

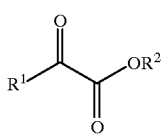

(I)

wherein $R^1$ is an optionally substituted lower alkyl group, an optionally substituted lower alkenyl group, an optionally substituted lower alkynyl group, an optionally substituted cycloalkyl group, an optionally substituted aryl group, or an optionally substituted heterocyclic group, and $R^2$ is an optionally substituted lower alkyl, which method is characterized in that the pyruvic acid compound of general formula (I) is reacted with a bisulfite of general formula (II):

$MHSO_3$ (II)

wherein M is $NH_4$ or an alkali metal, to give a bisulfite adduct of the pyruvic acid compound and the adduct is then decomposed with an acid.

The present invention further provides a process for producing a pyruvic acid compound of general formula (VIII):

(VIII)

wherein $R^3$ is an optionally substituted lower alkyl group or an optionally substituted aryl group, and $R^4$ is an optionally substituted lower alkyl group, with higher purity using the above purification method, as well as a bisulfite adduct of the pyruvic acid compound of general formula (VIII).

DETAILED DESCRIPTION OF THE INVENTION

It seems that the adduct of the pyruvic acid compound of general formula (I) with the bisulfite of formula (II) according to the present invention may have a structure such as a sulfonic acid (e.g., the structure disclosed in Bull. Chem. Soc. Jpn., 40, 2703(1967)), a sulfurous acid ester, or a molecular compound (e.g., the structure described in JP-A 3-34948), similarly to the case of an adduct of an aldehyde with a bisulfite (see, e.g., "Dai-Yuhkikagaku (4th ed.)", vol. 3, pp. 56–57, published on Aug. 30, 1964, Asakura-shoten; J. Org. Chem., 6, 888(1941)). The adduct of the pyruvic acid compound of general formula (I) with the bisulfite of general formula (II) according to the present invention may include those having the structures in all these cases.

In the pyruvic acid compounds of general formula (I) according to the present invention, the optionally substituted lower alkyl group in the substituent $R^1$ may include, for example, straight-chain or branched $C_1$–$C_8$ alkyl groups such as methyl, ethyl, n-propyl, isopropyl, n-butyl, isobutyl, sec-butyl, t-butyl, n-pentyl, neopentyl, n-hexyl, n-heptyl, and n-octyl groups.

These alkyl groups may optionally be substituted with one to four substituents selected from halogen atoms, lower alkoxycarbonyl, lower alkoxy, optionally substituted aryloxy, optionally substituted cycloalkyl, optionally substituted aryl, or optionally substituted heterocyclic groups.

The halogen atoms as used herein may include fluorine, chlorine, bromine, and iodine atoms. In the following description, the halogen atoms have the same meaning as described above.

The lower alkoxycarbonyl groups may include, for example, straight-chain or branched $C_1$–$C_6$ alkoxycarbonyl groups such as methoxycarbonyl, ethoxycarbonyl, n-propoxycarbonyl, isopropoxycarbonyl, n-butoxycarbonyl, isobutoxycarbonyl, sec-butoxycarbonyl, n-pentyloxycarbonyl, neopentyloxycarbonyl, and n-hexyloxycarbonyl groups.

The lower alkoxy groups may include, for example, straight-chain or branched $C_1$–$C_6$ alkoxy groups such as methoxy, ethoxy, n-propoxy, isopropoxy, n-butoxy, isobutoxy, sec-butoxy, n-pentyloxy, neopentyloxy, and n-hexyloxy groups. In the following description, the lower alkoxy groups have the same meaning as described above.

The optionally substituted aryloxy groups may include, for example, phenoxy, 1-naphthyloxy, and 2-naphthyloxy groups.

The optionally substituted cycloalkyl groups may include, for example, cyclic $C_3$–$C_8$ alkyl groups such as cyclopropyl, cyclobutyl, cyclopentyl, cyclohexyl, cycloheptyl, and cyclooctyl groups.

The optionally substituted aryl groups may include, for example, phenyl and naphthyl groups.

The optionally substituted heterocyclic groups may include, for example, monovalent groups of heterocycles containing one to three heteroatoms, such as furan, tetrahydrofuran, benzo[b]furan, pyrrole, pyrrolidine, pyridine, indole, imidazole, thiophene, and benzo[b]thiophene.

These aryloxy, cycloalkyl, aryl, and heterocyclic groups may optionally be further substituted with one to three substituents selected from halogen atoms, nitro, trifluoromethyl, lower alkyl, or lower alkoxy groups.

The lower alkyl groups as used herein may include, for example, straight-chain or branched $C_1$–$C_6$ alkyl groups such as methyl, ethyl, n-propyl, isopropyl, n-butyl, isobutyl, sec-butyl, t-butyl, n-pentyl, neopentyl, and n-hexyl groups.

In the following description, the optionally substituted cycloalkyl, optionally substituted aryl, optionally substituted aryloxy, or optionally substituted heterocyclic groups have the same meaning as described above.

When the lower alkyl group in the substituent $R^1$ is a methyl or ethyl group, it preferably has at least one substituent selected from halogen atoms, lower alkoxycarbonyl, lower alkoxy, optionally substituted aryloxy, optionally substituted cycloalkyl, optionally substituted aryl, or optionally substituted heterocyclic groups.

The optionally substituted lower alkenyl group in the substituent $R^1$ may include, for example, straight-chain or branched $C_2$–$C_6$ alkenyl groups such as vinyl, 1-methylvinyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 2-methyl-2-pentenyl, 1-hexenyl, 2-hexenyl, 3-hexenyl, 4-hexenyl, and 5-hexenyl groups.

These alkenyl groups may optionally be substituted with one to four substituents selected from halogen atoms, lower alkoxy, optionally substituted aryloxy, optionally substituted cycloalkyl, optionally substituted aryl, or optionally substituted heterocyclic groups. When the lower alkenyl group in the substituent $R^1$ is a vinyl group, it is preferably substituted as described above.

The optionally substituted lower alkynyl group in the substituent $R^1$ may include, for example, straight-chain or branched $C_2$–$C_6$ alkynyl groups such as ethynyl, 1-propynyl, 2-propynyl, 1-methyl-2-propynyl, 1-butynyl, 2-butynyl, 3-butynyl, 1-pentynyl, 2-pentynyl, 3-pentynyl, 4-pentynyl, 4-methyl-2-pentynyl, 1-hexynyl, 2-hexynyl, 3-hexynyl, 4-hexynyl, and 5-hexynyl groups.

These alkynyl groups may optionally be substituted with one to four substituents selected from the same halogen atoms, lower alkoxy, optionally substituted aryloxy, optionally substituted cycloalkyl, optionally substituted aryl, or optionally substituted heterocyclic groups as described above. When the lower alkynyl group in the substituent $R^1$ is an ethynyl group, it is preferably substituted as described above.

The optionally substituted cycloalkyl, optionally substituted aryl, or optionally substituted heterocyclic groups in the substituent $R^1$ may include the same groups as described above.

The optionally substituted lower alkyl group represented by substituent $R^2$ may include, for example, straight-chain or branched $C_1$–$C_6$ alkyl groups such as methyl, ethyl, n-propyl, isopropyl, n-butyl, isobutyl, sec-butyl, t-butyl, n-pentyl, neopentyl, and n-hexyl groups.

These lower alkyl groups may optionally be substituted with one to two optionally substituted aryl groups, and the aryl group may include, for example, phenyl and p-nitrophenyl groups. The lower alkyl groups substituted with the aryl group may include, for example, benzyl, p-nitrobenzyl, and 2-phenylethyl groups.

Specific examples of the pyruvic acid compound are methyl 3-cyclohexyl-2-oxopropanoate, methyl 3-(4-methoxycyclohexyl)-2-oxopropanoate, methyl 2-oxo-3-phenylpropanoate, methyl 3-(2-fluorophenyl)-2-oxopropanoate, methyl 3-(3-fluorophenyl)-2-oxopropanoate, methyl 3-(4-fluorophenyl)-2-oxopropanoate, methyl 3-(2-chlorophenyl)-2-oxopropanoate, methyl 3-(3-chlorophenyl)-2- oxopropanoate, methyl 3-(4-chlorophenyl)-2-oxopropanoate, methyl 3-(2-bromophenyl)-2-oxopropanoate, methyl 3-(3-bromophenyl)-2-oxopropanoate, methyl 3-(4-bromophenyl)-2-oxopropanoate, methyl 3-(2-iodophenyl)-2-oxopropanoate, methyl 3-(2,5-difluorophenyl)-2-oxopropanoate, methyl 3-(2,6-difluorophenyl)-2-oxopropanoate, methyl 3-(3,4-difluorophenyl)-2-oxopropanoate, methyl 3-(3,5-difluorophenyl)-2-oxopropanoate, methyl 3-(2,4-dichlorophenyl)-2-oxopropanoate, methyl 3-(2,6-dichlorophenyl)-2-oxopropanoate, methyl 3-(3,4-dichlorophenyl)-2-oxopropanoate, methyl 3-(2-chloro-6-fluorophenyl)-2-oxopropanoate, methyl 3-(2-nitrophenyl)-2-oxopropanoate, methyl 3-(3-nitrophenyl)-2-oxopropanoate, methyl 3-(4-nitrophenyl)-2-oxopropanoate, methyl 3-(2,4-dinitrophenyl)-2-oxopropanoate, methyl 3-(3,5-dinitrophenyl)-2-oxopropanoate, methyl 3-(4-chloro-2-nitrophenyl)-2-oxopropanoate, methyl 2-oxo-3-(2-trifluoromethylphenyl)propanoate, methyl 2-oxo-3-(3-trifluoromethylphenyl)propanoate, methyl 2-oxo-3-(4-trifluoromethylphenyl)propanoate, methyl 3-(3,5-bistrifluoromethylphenyl)-2-oxopropanoate, methyl 3-(2-methylphenyl)-2-oxopropanoate, methyl 3-(3-methylphenyl)-2-oxopropanoate, methyl 3-(4-methylphenyl)-2-oxopropanoate, methyl 3-(4-ethylphenyl)-2-oxopropanoate, methyl 3-(4-isopropylphenyl)-2-oxopropanoate, methyl 3-(4-t-butylphenyl)-2-oxopropanoate, methyl 3-(2,5-dimethylphenyl)-2-oxopropanoate, methyl 3-(3,4-dimethylphenyl)-2-oxopropanoate, methyl 3-(2-methyl-3-nitrophenyl)-2-oxopropanoate, methyl 3-(5-methyl-2-nitrophenyl)-2-oxopropanoate, methyl 2-oxo-3-(2,4,6-trimethylphenyl)propanoate, methyl 3-(2-methoxyphenyl)-2-oxopropanoate, methyl 3-(3-methoxyphenyl)-2-oxopropanoate, methyl 3-(4-methoxyphenyl)-2-oxopropanoate, methyl 3-(2-methoxy-5-nitrophenyl)-2-oxopropanoate, methyl 3-(1-naphthyl)-2-oxopropanoate, methyl 3-(2-naphthyl)-2-oxopropanoate, methyl 3-(3-indolyl)-2-oxopropanoate, methyl 3-methyl-2-oxobutanoate, methyl 3,3-dimethyl-2-oxobutanoate, methyl 4-methoxy-2-oxobutanoate, methyl 2-oxo-3-phenylbutanoate, methyl 3-methyl-2-oxo-4-phenylbutanoate, methyl 2-oxo-4-phenylbutanoate, methyl 4-(4-fluorophenyl)-2-oxobutanoate, methyl 4-(3-chlorophenyl)-2-oxobutanoate, methyl 4-(4-chlorophenyl)-2-oxobutanoate, methyl 4-(2-bromophenyl)-2-oxobutanoate, methyl 4-(2-nitrophenyl)-2-oxobutanoate, methyl 4-(4-nitrophenyl)-2-oxobutanoate, methyl 4-(4-chloro-2-nitrophenyl)-2-oxobutanoate, methyl 4-(4-bromo-2-nitrophenyl)-2-oxobutanoate, methyl 2-oxo-4-(3-trifluoromethylphenyl)butanoate, methyl 4-(2-methylphenyl)-2-oxobutanoate, methyl 4-(2,4-dimethylphenyl)-2-oxobutanoate, methyl 4-(2-methoxyphenyl)-2-oxobutanoate, methyl 4-(4-methoxyphenyl)-2-oxobutanoate, methyl 4-(2,5-dimethoxyphenyl)-2-oxobutanoate, methyl 4-(3,4-dimethoxyphenyl)-2-oxobutanoate, methyl 4-(1-naphthyl)-2-oxobutanoate, methyl 4-(2-nitro-1-naphthyl)-2-oxobutanoate, methyl 4-(2-naphthyl)-2-oxobutanoate, methyl 4-(1-chloro-2-naphthyl)-2-oxobutanoate, methyl 4-(1-bromo-2-naphthyl)-2-oxobutanoate, methyl 4-(1-nitro-2-naphthyl)-2-oxobutanoate, methyl 2-oxopentanoate, methyl 3-methyl-2-oxopentanoate, methyl 5-cyclohexyl-2-oxopentanoate, methyl 2-oxo-5-phenylpentanoate, methyl 5-(3-chlorophenyl)-2-oxopentanoate, methyl 5-(3-methoxyphenyl)-2-oxopentanoate, methyl 5-(4-methoxyphenyl)-2-oxopentanoate, methyl 5,5-diphenyl-2-oxopentanoate, methyl 5-methoxy-2-oxo-5-phenylpentanoate, methyl 5-(4-chlorophenyl)-5-methoxy-2-oxopentanoate, methyl 5-isopropoxy-2-oxo-5-phenylpentanoate, methyl 5-isopropoxy-5-(4-methylphenyl)-2-oxopentanoate, methyl 2-oxo-5-phenoxypentanoate, methyl 5-(4-fluorophenoxy)-2-oxopentanoate, methyl 5-(2-bromo-4-methylphenoxy)-2-oxopentanoate, methyl 5-(2,6-dibromo-4-methylphenoxy)-2-oxopentanoate, methyl 2-oxohexanoate, methyl 5-methyl-2-oxohexanoate, methyl 5,5-dimethyl-2-oxohexanoate, methyl 2-oxo-5-phenylhexanoate, methyl 2-oxo-6-phenylhexanoate, methyl 2-oxo-6-phenoxyhexanoate, methyl 6-(2-methylphenoxy)-2-oxohexanoate, methyl 6-(3-methylphenoxy)-2-oxohexanoate, methyl 6-(4-methylphenoxy)-2-oxohexanoate, methyl 6-(4-nitrophenoxy)-2-oxohexanoate, methyl 6-(2,5-dimethylphenoxy)-2-oxohexanoate, methyl 2-oxoheptanoate, methyl 7-chloro-2-oxoheptanoate, methyl 7-bromo-2-oxoheptanoate, methyl 6-methyl-2-oxoheptanoate, methyl 2-oxo-7-phenylheptanoate, methyl 2-oxo-7-phenoxyheptanoate, methyl 7-(4-t-butylphenoxy)-2-oxoheptanoate, methyl 2-oxooctanoate, methyl 7-methyl-2-oxooctanoate, methyl 2-oxo-8-phenyloctanoate, methyl 2-oxononanoate, methyl 8-methyl-2-oxononanoate, methyl 2-oxodecanoate, methyl 2-oxo-10-phenoxydecanoate, methyl 3-methyl-2-oxo-3-butenoate, methyl 2-oxo-4-phenyl-3-butenoate, methyl 2-oxo-4-pentenoate, methyl 4-chloro-2-oxo-4-pentenoate, methyl 4-methyl-2-oxo-4-pentenoate, methyl 2-oxo-4-hexenoate, methyl 5-methyl-2-oxo-4-hexenoate, methyl 2-oxo-4-phenyl-3-butynoate, methyl 2-oxo-3-pentynoate, methyl 2-oxo-4-hexynoate, methyl 2-oxo-3-hexynoate, methyl 6-methoxy-2-oxo-3-hexynoate, methyl 7-ethoxy-2-oxo-3-heptynoate, methyl 2-cyclopropyl-2-oxoethanoate, methyl 2-cyclobutyl-2-oxoethanoate, methyl 2-cyclopentyl-2-oxoethanoate, methyl 2-cyclohexyl-2-oxoethanoate, methyl 2-cycloheptyl-2-oxoethanoate, methyl 2-cyclooctyl-2-oxoethanoate, methyl 2-oxo-2-phenylethanoate, methyl 2-(2-methylphenyl)-2-oxoethanoate, methyl 2-(4-methoxyphenyl)-2-oxoethanoate, methyl 2-(1-naphthyl)-2-oxoethanoate, methyl 2-(2-naphthyl)-2-oxoethanoate, methyl 2-(2-furyl)-2-oxoethanoate, methyl 2-(2-benzo[b]furyl)-2-oxoethanoate, methyl 2-oxo-2-(2-pyrrolyl)ethanoate, methyl 2-(3-indolyl)-2-oxoethanoate, methyl 2-oxo-2-(2-thienyl)ethanoate, methyl 2-(2-benzo[b]thienyl)-2-oxoethanoate, methyl 3-(benzothiazol-2-yl)-2-oxopropanoate, ethyl 3-cyclohexyl-2-oxopropanoate, ethyl 3-(4-methoxycyclohexyl)-2-oxopropanoate, ethyl 2-oxo-3-phenylpropanoate, ethyl 3-(2-fluorophenyl)-2-oxopropanoate, ethyl 3-(3-fluorophenyl)-2-oxopropanoate, ethyl 3-(4-fluorophenyl)-2-oxopropanoate, ethyl 3-(2-chlorophenyl)-2-oxopropanoate, ethyl 3-(3-chlorophenyl)-2-oxopropanoate, ethyl 3-(4-chlorophenyl)-2-oxopropanoate, ethyl 3-(2-bromophenyl)-2-oxopropanoate, ethyl 3-(3-bromophenyl)-2-oxopropanoate, ethyl 3-(4-bromophenyl)-2-oxopropanoate, ethyl 3-(2-iodophenyl)-2-oxopropanoate, ethyl 3-(2,5-difluorophenyl)-2-oxopropanoate, ethyl 3-(2,6-difluorophenyl)-2-oxopropanoate, ethyl 3-(3,4-difluorophenyl)-2-oxopropanoate, ethyl 3-(3,5-difluorophenyl)-2-oxopropanoate, ethyl 3-(2,4-dichlorophenyl)-2-oxopropanoate, ethyl 3-(2,6-dichlorophenyl)-2-oxopropanoate, ethyl 3-(3,4-dichlorophenyl)-2-oxopropanoate, ethyl 3-(2-chloro-6-fluorophenyl)-2-oxopropanoate, ethyl 3-(2-nitrophenyl)-2-oxopropanoate, ethyl 3-(3-nitrophenyl)-2-oxopropanoate, ethyl 3-(4-nitrophenyl)-2-oxopropanoate, ethyl 3-(2,4-dinitrophenyl)-2-oxopropanoate, ethyl 3-(3,5-dinitrophenyl)-2- oxopropanoate, ethyl 3-(4-chloro-2-nitrophenyl)-2-oxopropanoate, ethyl 2-oxo-3-(2-trifluoromethylphenyl)propanoate, ethyl 2-oxo-3-(3-trifluoromethylphenyl)propanoate, ethyl 2-oxo-3-(4-trifluoromethylphenyl)propanoate, ethyl 3-(3,5-bistrifluoromethylphenyl)-2-oxopropanoate, ethyl 3-(2-methylphenyl)-2-oxopropanoate, ethyl 3-(3-methylphenyl)-2-oxopropanoate, ethyl 3-(4-methylphenyl)-2-oxopropanoate, ethyl 3-(4-ethylphenyl)-2-oxopropanoate, ethyl 3-(4-isopropylphenyl)-2-oxopropanoate, ethyl 3-(4-t-butylphenyl)-2-oxopropanoate, ethyl 3-(2,5-dimethylphenyl)-2-oxopropanoate, ethyl 3-(3,4-dimethylphenyl)-2-oxopropanoate, ethyl 3-(2-methyl-3-nitrophenyl)-2-oxopropanoate, ethyl 3-(5-methyl-2-nitrophenyl)-2-oxopropanoate, ethyl 2-oxo-3-(2,4,6-trimethylphenyl)propanoate, ethyl 3-(2-methoxyphenyl)-2-oxopropanoate, ethyl 3-(3-methoxyphenyl)-2-oxopropanoate, ethyl 3-(4-methoxyphenyl)-2-oxopropanoate, ethyl 3-(2-methoxy-5-nitrophenyl)-2-oxopropanoate, ethyl 3-(1-naphthyl)-2-oxopropanoate, ethyl 3-(2-naphthyl)-2-oxopropanoate, ethyl 3-(3-indolyl)-2-oxopropanoate, ethyl 3-methyl-2-oxobutanoate, ethyl 3,3-dimethyl-2-oxobutanoate, ethyl 4-methoxy-2-oxobutanoate, ethyl 2-oxo-3-phenylbutanoate, ethyl 3-methyl-2-oxo-4-phenylbutanoate, ethyl 2-oxo-4-phenylbutanoate, ethyl 4-(4-fluorophenyl)-2-oxobutanoate, ethyl 4-(3-chlorophenyl)-2-oxobutanoate, ethyl 4-(4-chlorophenyl)-2-oxobutanoate, ethyl 4-(2-bromophenyl)-2-oxobutanoate, ethyl 4-(2-nitrophenyl)-2-oxobutanoate, ethyl 4-(4-nitrophenyl)-2-oxobutanoate, ethyl 4-(4-chloro-2-nitrophenyl)-2-oxobutanoate, ethyl 4-(4-bromo-2-nitrophenyl)-2-oxobutanoate, ethyl 2-oxo-4-(3-trifluoromethylphenyl)butanoate, ethyl (2-methoxyphenyl)-2-oxobutanoate, ethyl 4-(2,4-dimethylphenyl)-2-oxobutanoate ethyl 4-(2-methoxyphenyl)-2-oxobutanoate, ethyl 4-(4-methoxyphenyl)-2-oxobutanoate, ethyl 4-(2,5-dimethoxyphenyl)-2-oxobutanoate, ethyl 4-(3,4-dimethoxyphenyl)-2-oxobutanoate, ethyl 4-(1-naphthyl)-2-oxobutanoate, ethyl 4-(2-nitro-1-naphthyl)-2-oxobutanoate, ethyl 4-(2-naphthyl)-2-oxobutanoate, ethyl 4-(1-chloro-2-naphthyl)-2-oxobutanoate, ethyl 4-(1-bromo-2-naphthyl)-2-oxobutanoate, ethyl 4-(1-nitro-2-naphthyl)-2-oxobutanoate, ethyl 2-oxopentanoate, ethyl 3-methyl-2-oxopentanoate, ethyl 2-oxopentanoate, ethyl 5-cyclohexyl-2-oxopentanoate, ethyl 2-oxo-5-phenylpentanoate, ethyl 5-(3-chlorophenyl)-2-oxopentanoate, ethyl 5-(3-methoxyphenyl)-2-oxopentanoate, ethyl 5-(4-methoxyphenyl)-2-oxopentanoate, ethyl 5,5-diphenyl-2-oxopentanoate, ethyl 5-methoxy-2-oxo-5-phenylpentanoate, ethyl 5-(4-chlorophenyl)-5-methoxy-2-oxopentanoate, ethyl 5-isopropoxy-2-oxo-5-phenylpentanoate, ethyl 5-isopropoxy-5-(4-methylphenyl)-2-oxopentanoate, ethyl 2-oxo-5-phenoxypentanoate, ethyl 5-(4-fluorophenoxy)-2-oxopentanoate, ethyl 5-(2-bromo-4-methylphenoxy)-2-oxopentanoate, ethyl 5-(2,6-dibromo-4-methylphenoxy)-2-oxopentanoate, ethyl 2-oxohexanoate, ethyl 5-methyl-2-oxohexanoate, ethyl 5,5-dimethyl-2-oxohexanoate, ethyl 2-oxo-5-phenylhexanoate, ethyl 2-oxo-6-phenylhexanoate, ethyl 2-oxo-6-phenoxyhexanoate, ethyl 6-(2-methylphenoxy)-2-oxohexanoate, ethyl 6-(3-methylphenoxy)-2-oxohexanoate, ethyl 6-(4-methylphenoxy)-2-oxohexanoate, ethyl 6-(4-nitrophenoxy)-2-oxohexanoate, ethyl 6-(2,5-dimethylphenoxy)-2-oxohexanoate, ethyl 2-oxoheptanoate, ethyl 7-chloro-2-oxoheptanoate, ethyl 7-bromo-2-oxoheptanoate, ethyl 6-methyl-2-oxoheptanoate, ethyl 2-oxo-7-phenylheptanoate, ethyl 2-oxo-7-phenoxyheptanoate, ethyl 7-(4-t-butylphenoxy)-2-oxoheptanoate, ethyl 2-oxooctanoate, ethyl 7-methyl-2-oxooctanoate, ethyl 2-oxo-8-phenyloctanoate, ethyl 2-oxononanoate, ethyl 8-methyl-2-oxononanoate, ethyl 2-oxodecanoate, ethyl 2-oxo-10-phenoxydecanoate, ethyl 3-methyl-2-oxo-3-butenoate, ethyl 2-oxo-4-phenyl-3-butenoate, ethyl 2-oxo-4-pentenoate, ethyl 4-chloro-2-oxo-4-pentenoate, ethyl 4-methyl-2-oxo-4-pentenoate, ethyl 2-oxo-4-hexenoate, ethyl 5-methyl-2-oxo-4-hexenoate, ethyl 2-oxo-4-phenyl-3-butynoate, ethyl 2-oxo-3-pentynoate, ethyl 2-oxo-4-hexynoate, ethyl 2-oxo-3-hexynoate, ethyl 6-methoxy-2-oxo-3-hexynoate, ethyl 7-ethoxy-2-oxo-3-heptynoate, ethyl 2-cyclopropyl-2-oxoethanoate, ethyl 2-cyclobutyl-2-oxoethanoate, ethyl 2-cyclopentyl-2-oxoethanoate, ethyl 2-cyclohexyl-2-oxoethanoate, ethyl 2-cycloheptyl-2-oxoethanoate, ethyl 2-cyclooctyl-2-oxoethanoate, ethyl 2-oxo-2-phenylethanoate, ethyl 2-(2-methylphenyl)-2-oxoethanoate, ethyl 2-(4-methoxyphenyl)-2-oxoethanoate, ethyl 2-(1-naphthyl)-2-oxoethanoate, ethyl 2-(2-naphthyl)-2-oxoethanoate, ethyl 2-(2-furyl)-2-oxoethanoate, ethyl 2-(2-benzo[b]furyl)-2-oxoethanoate, ethyl 2-oxo-2-(2-pyrrolyl)ethanoate, ethyl 2-(3-indolyl)-2-oxoethanoate, ethyl 2-oxo-2-(2-thienyl)ethanoate, ethyl 2-(2-benzo[b]thienyl)-2-oxoethanoate, ethyl 3-(benzothiazol-2-yl)-2-oxopropanoate, isopropyl 3-cyclohexyl-2-oxopropanoate, isopropyl 3-(4-methoxycyclohexyl)-2-oxopropanoate, isopropyl 2-oxo-3-phenylpropanoate, isopropyl 3-(2-fluorophenyl)-2-oxopropanoate, isopropyl 3-(3-fluorophenyl)-2-oxopropanoate, isopropyl 3-(4-fluorophenyl)-2-oxopropanoate, isopropyl 3-(2-chlorophenyl)-2-oxopropanoate, isopropyl 3-(3-chlorophenyl)-2-oxopropanoate, isopropyl 3-(4-chlorophenyl)-2-oxopropanoate, isopropyl 3-(2-bromophenyl)-2-oxopropanoate, isopropyl 3-(3-bromophenyl)-2-oxopropanoate, isopropyl 3-(4-bromophenyl)-2-oxopropanoate, isopropyl 3-(2-iodophenyl)-2-oxopropanoate, isopropyl 3-(2,5-difluorophenyl)-2-oxopropanoate, isopropyl 3-(2,6-difluorophenyl)-2-oxopropanoate, isopropyl 3-(3,4-difluorophenyl)-2-oxopropanoate, isopropyl 3-(3,5-difluorophenyl)-2-oxopropanoate, isopropyl 3-(2,4-dichlorophenyl)-2-oxopropanoate, isopropyl 3-(2,6-dichlorophenyl)-2-oxopropanoate, isopropyl 3-(3,4-dichlorophenyl)-2-oxopropanoate, isopropyl 3-(2-chloro-6-fluorophenyl)-2-oxopropanoate, isopropyl 3-(2-nitrophenyl)-2-oxopropanoate, isopropyl 3-(3-nitrophenyl)-2-oxopropanoate, isopropyl 3-(4-nitrophenyl)-2-oxopropanoate, isopropyl 3-(2,4-dinitrophenyl)-2-oxopropanoate, isopropyl 3-(3,5-dinitrophenyl)-2-oxopropanoate, isopropyl 3-(4-chloro-2-nitrophenyl)-2-oxopropanoate, isopropyl 2-oxo-3-(2-trifluoromethylphenyl)propanoate, isopropyl 2-oxo-3-(3-trifluoromethylphenyl)propanoate, isopropyl 2-oxo-3-(4-trifluoromethylphenyl)propanoate, isopropyl 3-(3,5-bistrifluoromethylphenyl)-2-oxopropanoate, isopropyl 3-(2-methylphenyl)-2-oxopropanoate, isopropyl 3-(3-methylphenyl)-2-oxopropanoate, isopropyl 3-(4-methylphenyl)-2-oxopropanoate, isopropyl 3-(4-ethylphenyl)-2-oxopropanoate, isopropyl 3-(4-isopropylphenyl)-2-oxopropanoate, isopropyl 3-(4-t-butylphenyl)-2-oxopropanoate, isopropyl 3-(2,5-dimethylphenyl)-2-oxopropanoate, isopropyl 3-(3,4-dimethylphenyl)-2-oxopropanoate, isopropyl 3-(2-methyl-3-nitrophenyl)-2-oxopropanoate, isopropyl 3-(5-methyl-2-nitrophenyl)-2-oxopropanoate, isopropyl 2-oxo-3-(2,4,6-trimethylphenyl)propanoate, isopropyl 3-(2-methoxyphenyl)-2-oxopropanoate, isopropyl 3-(3-methoxyphenyl)-2-oxopropanoate, isopropyl 3-(4- methoxyphenyl)-2-oxopropanoate, isopropyl 3-(2-methoxy-5-nitrophenyl)-2-oxopropanoate, isopropyl 3-(1-naphthyl)-2-oxopropanoate, isopropyl 3-(2-naphthyl)-2-oxopropanoate, isopropyl 3-(3-indolyl)-2-oxopropanoate, isopropyl 3-methyl-2-oxobutanoate, isopropyl 3,3-dimethyl-2-oxobutanoate, isopropyl 4-methoxy-2-oxobutanoate, isopropyl 2-oxo-3-phenylbutanoate, isopropyl 3-methyl-2-oxo-4-phenylbutanoate, isopropyl 2-oxo-4-phenylbutanoate, isopropyl 4-(4-fluorophenyl)-2-oxobutanoate, isopropyl 4-(3-chlorophenyl)-2-oxobutanoate, isopropyl 4-(4-chlorophenyl)-2-oxobutanoate, isopropyl 4-(2-bromophenyl)-2-oxobutanoate, isopropyl 4-(2-nitrophenyl)-2-oxobutanoate, isopropyl 4-(4-nitrophenyl)-2-oxobutanoate, isopropyl 4-(4-chloro-2-nitrophenyl)-2-oxobutanoate, isopropyl 4-(4-bromo-2-nitrophenyl)-2-oxobutanoate, isopropyl 2-oxo-4-(3-trifluoromethylphenyl)butanoate, isopropyl 4-(2-methylphenyl)-2-oxobutanoate, isopropyl 4-(2,4-dimethylphenyl)-2-oxobutanoate, isopropyl 4-(2-methoxyphenyl)-2-oxobutanoate, isopropyl 4-(4-methoxyphenyl)-2-oxobutanoate, isopropyl 4-(2,5-dimethoxyphenyl)-2-oxobutanoate, isopropyl 4-(3,4-dimethoxyphenyl)-2-oxobutanoate, isopropyl 4-(1-naphthyl)-2-oxobutanoate, isopropyl 4-(2-nitro-1-naphthyl)-2-oxobutanoate, isopropyl 4-(2-naphthyl)-2-oxobutanoate, isopropyl 4-(1-chloro-2-naphthyl)-2-oxobutanoate, isopropyl 4-(1-bromo-2-naphthyl)-2-oxobutanoate, isopropyl 4-(1-nitro-2-naphthyl)-2-oxobutanoate, isopropyl 2-oxopentanoate, isopropyl 3-methyl-2-oxopentanoate, isopropyl 2-oxopentanoate, isopropyl 5-cyclohexyl-2-oxopentanoate, isopropyl 2-oxo-5-phenylpentanoate, isopropyl 5-(3-chlorophenyl)-2-oxopentanoate, isopropyl 5-(3-methoxyphenyl)-2-oxopentanoate, isopropyl 5-(4-methoxyphenyl)-2-oxopentanoate, isopropyl 5,5-diphenyl-2-oxopentanoate, isopropyl 5-methoxy-2-oxo-5-phenylpentanoate, isopropyl 5-(4-chlorophenyl)-5-methoxy-2-oxopentanoate, isopropyl 5-isopropoxy-2-oxo-5-phenylpentanoate, isopropyl 5-isopropoxy-5-(4-methylphenyl)-2-oxopentanoate, isopropyl 2-oxo-5-phenoxypentanoate, isopropyl 5-(4-fluorophenoxy)-2-oxopentanoate, isopropyl 5-(2-bromo-4-methylphenoxy)-2-oxopentanoate, isopropyl 5-(2,6-dibromo-4-methylphenoxy)-2-oxopentanoate, isopropyl 2-oxohexanoate, isopropyl 5-methyl-2-oxohexanoate, isopropyl 5,5-dimethyl-2-oxohexanoate, isopropyl 2-oxo-5-phenylhexanoate, isopropyl 2-oxo-6-phenylhexanoate, isopropyl 2-oxo-6-phenoxyhexanoate, isopropyl 6-(2-methylphenoxy)-2-oxohexanoate, isopropyl 6-(3-methylphenoxy)-2-oxohexanoate, isopropyl 6-(4-methylphenoxy)-2-oxohexanoate, isopropyl 6-(4-nitrophenoxy)-2-oxohexanoate, isopropyl 6-(2,5-dimethylphenoxy)-2-oxohexanoate, isopropyl 2-oxoheptanoate, isopropyl 7-chloro-2-oxoheptanoate, isopropyl 7-bromo-2-oxoheptanoate, isopropyl 6-methyl-2-oxoheptanoate, isopropyl 2-oxo-7-phenylheptanoate, isopropyl 2-oxo-7-phenoxyheptanoate, isopropyl 7-(4-t-butylphenoxy)-2-oxoheptanoate, isopropyl 2-oxooctanoate, isopropyl 7-methyl-2-oxooctanoate, isopropyl 2-oxo-8-phenyloctanoate, isopropyl 2-oxononanoate, isopropyl 8-methyl-2-oxononanoate, isopropyl 2-oxodecanoate, isopropyl 2-oxo-10-phenoxydecanoate, isopropyl 3-methyl-2-oxo-3-butenoate, isopropyl 2-oxo-4-phenyl-3-butenoate, isopropyl 2-oxo-4-pentenoate, isopropyl 4-chloro-2-oxo-4-pentenoate, isopropyl 4-methyl-2-oxo-4-pentenoate, isopropyl 2-oxo-4-hexenoate, isopropyl 5-methyl-2-oxo-4-hexenoate, isopropyl 2-oxo-4-phenyl-3-butynoate, isopropyl 2-oxo-3-pentynoate, isopropyl 2-oxo-4-hexynoate, isopropyl 2-oxo-3-hexynoate, isopropyl 6-methoxy-2-oxo-3-hexynoate, isopropyl 7-ethoxy-2-oxo-3-heptynoate, isopropyl 2-cyclopropyl-2-oxoethanoate, isopropyl 2-cyclobutyl-2-oxoethanoate, isopropyl 2-cyclopentyl-2-oxoethanoate, isopropyl 2-cyclohexyl-2-oxoethanoate, isopropyl 2-cycloheptyl-2-oxoethanoate, isopropyl 2-cyclooctyl-2-oxoethanoate, isopropyl 2-oxo-2-phenylethanoate, isopropyl 2-(2-methylphenyl)-2-oxoethanoate, isopropyl 2-(4-methoxyphenyl)-2-oxoethanoate, isopropyl 2-(1-naphthyl)-2-oxoethanoate, isopropyl 2-(2-naphthyl)-2-oxoethanoate, isopropyl 2-(2-furyl)-2-oxoethanoate, isopropyl 2-(2-benzo[b]furyl)-2-oxoethanoate, isopropyl 2-oxo- 2-(2-pyrrolyl)ethanoate, osopropyl 2-(3-indolyl)-2-oxoethanoate, isopropyl 2-oxo-2-(2-thienyl)ethanoate, isopropyl 2-(2-benzo[b]thienyl)-2-oxoethanoate, isopropyl 3-(benzothiazol-2-yl)-2-oxopropanoate, benzyl 3-cyclohexyl-2-oxopropanoate, benzyl 3-(4-methoxycyclohexyl)-2-oxopropanoate, benzyl 2-oxo-3-phenylpropanoate, benzyl 3-(2-fluorophenyl)-2-oxopropanoate, benzyl 3-(3-fluorophenyl)-2-oxopropanoate, benzyl 3-(4-fluorophenyl)-2-oxopropanoate, benzyl 3-(2-chlorophenyl)-2-oxopropanoate, benzyl 3-(3-chlorophenyl)-2-oxopropanoate, benzyl 3-(4-chlorophenyl)-2-oxopropanoate, benzyl 3-(2-bromophenyl)-2-oxopropanoate, benzyl 3-(3-bromophenyl)-2-oxopropanoate, benzyl 3-(4-bromophenyl)-2-oxopropanoate, benzyl 3-(2-iodophenyl)-2-oxopropanoate, benzyl 3-(2,5-difluorophenyl)-2-oxopropanoate, benzyl 3-(2,6-difluorophenyl)-2-oxopropanoate, benzyl 3-(3,4-difluorophenyl)-2-oxopropanoate, benzyl 3-(3,5-difluorophenyl)-2-oxopropanoate, benzyl 3-(2,4-dichlorophenyl)-2-oxopropanoate, benzyl 3-(2,6-dichlorophenyl)-2-oxopropanoate, benzyl 3-(3,4-dichlorophenyl)-2-oxopropanoate, benzyl 3-(2-chloro-6-fluorophenyl)-2-oxopropanoate, benzyl 3-(2-nitrophenyl)-2-oxopropanoate, benzyl 3-(3-nitrophenyl)-2-oxopropanoate, benzyl 3-(4-nitrophenyl)-2-oxopropanoate, benzyl 3-(2,4-dinitrophenyl)-2-oxopropanoate, benzyl 3-(3,5-dinitrophenyl)-2-oxopropanoate, benzyl 3-(4-chloro-2-nitrophenyl)-2-oxopropanoate, benzyl 2-oxo-3-(2-trifluoromethylphenyl)propanoate, benzyl 2-oxo-3-(3-trifluoromethylphenyl)propanoate, benzyl 2-oxo-3-(4-trifluoromethylphenyl)propanoate, benzyl 3-(3,5-bistrifluoromethylphenyl)-2-oxopropanoate, benzyl 3-(2-methylphenyl)-2-oxopropanoate, benzyl 3-(3-methylphenyl)-2-oxopropanoate, benzyl 3-(4-methylphenyl)-2-oxopropanoate, benzyl 3-(4-ethylphenyl)-2-oxopropanoate, benzyl 3-(4-isopropylphenyl)-2-oxopropanoate, benzyl 3-(4-t-butylphenyl)-2-oxopropanoate, benzyl 3-(2,5-dimethylphenyl)-2-oxopropanoate, benzyl 3-(3,4-dimethylphenyl)-2-oxopropanoate, benzyl 3-(2-methyl-3-nitrophenyl)-2-oxopropanoate, benzyl 3-(5-methyl-2-nitrophenyl)-2-oxopropanoate, benzyl 2-oxo-3-(2,4,6-trimethylphenyl)propanoate, benzyl 3-(2-methoxyphenyl)-2-oxopropanoate, benzyl 3-(3-methoxyphenyl)-2-oxopropanoate, benzyl 3-(4-methoxyphenyl)-2-oxopropanoate, benzyl 3-(2-methoxy-5-nitrophenyl)-2-oxopropanoate, benzyl 3-(1-naphthyl)-2-oxopropanoate, benzyl 3-(2-naphthyl)-2-oxopropanoate, benzyl 3-(3-indolyl)-2-oxopropanoate, t-butyl 3-methyl-2-oxobutanoate, benzyl 3,3-dimethyl-2-oxobutanoate, benzyl 4-methoxy-2-oxobutanoate, benzyl 2-oxo-3-phenylbutanoate, benzyl 3-methyl-2-oxo-4-phenylbutanoate, benzyl 2-oxo-4-phenylbutanoate, benzyl 4-(4-fluorophenyl)-2-oxobutanoate, benzyl 4-(3-chlorophenyl)-2-oxobutanoate, benzyl 4-(4-chlorophenyl)-

2-oxobutanoate, benzyl 4-(2-bromophenyl)-2-oxobutanoate, benzyl 4-(2-nitrophenyl)-2-oxobutanoate, benzyl 4-(4-nitrophenyl)-2-oxobutanoate, benzyl 4-(4-chloro-2-nitrophenyl)-2-oxobutanoate, benzyl 4-(4-bromo-2-nitrophenyl)-2-oxobutanoate, benzyl 4-(2-methylphenyl)-2-oxobutanoate, benzyl 2-oxo-4-(3-trifluoromethylphenyl) butanoate, benzyl 4-(2,4-dimethylphenyl)-2-oxobutanoate, benzyl 4-(2-methoxyphenyl)-2-oxobutanoate, benzyl 4-(4-methoxyphenyl)-2-oxobutanoate, benzyl 4-(2,5-dimethoxyphenyl)-2-oxobutanoate, benzyl 4-(3,4-dimethoxyphenyl)-2-oxobutanoate, benzyl 4-(1-naphthyl)-2-oxobutanoate, benzyl 4-(2-nitro-1-naphthyl)-2-oxobutanoate, benzyl 4-(2-naphthyl)-2-oxobutanoate, benzyl 4-(1-chloro-2-naphthyl)-2-oxobutanoate, benzyl 4-(1-bromo-2-naphthyl)-2-oxobutanoate, benzyl 4-(1-nitro-2-naphthyl)-2-oxobutanoate, benzyl 2-oxopentanoate, benzyl 3-methyl-2-oxopentanoate, benzyl 2-oxopentanoate, benzyl 5-cyclohexyl-2-oxopentanoate, benzyl 2-oxo-5-phenylpentanoate, benzyl 5-(3-chlorophenyl)-2-oxopentanoate, benzyl 5-(3-methoxyphenyl)-2-oxopentanoate, benzyl 5-(4-methoxyphenyl)-2-oxopentanoate, benzyl 5,5-diphenyl-2-oxopentanoate, benzyl 5-methoxy-2-oxo-5-phenylpentanoate, benzyl 5-(4-chlorophenyl)-5-methoxy-2-oxopentanoate, benzyl 5-isopropoxy-2-oxo-5-phenylpentanoate, benzyl 5-isopropoxy-5-(4-methylphenyl)-2-oxopentanoate, benzyl 2-oxo-5-phenoxypentanoate, benzyl 5-(4-fluorophenoxy-)-2-oxopentanoate, benzyl 5-(2-bromo-4-methylphenoxy)-2-oxopentanoate, benzyl 5-(2,6-dibromo-4-methylphenoxy)-2-oxopentanoate, benzyl 2-oxohexanoate, benzyl 5-methyl-2-oxohexanoate, benzyl 5,5-dimethyl-2-oxohexanoate, benzyl 2-oxo-5-phenylhexanoate, benzyl 2-oxo-6-phenylhexanoate, benzyl 2-oxo-6-phenoxyhexanoate, benzyl 6-(2-methylphenoxy)-2-oxohexanoate, benzyl 6-(3-methylphenoxy)-2-oxohexanoate, benzyl 6-(4-methylphenoxy)-2-oxohexanoate, benzyl 6-(4-nitrophenoxy)-2-oxohexanoate, benzyl 6-(2,5-dimethylphenoxy)-2-oxohexanoate, benzyl 2-oxoheptanoate, benzyl 7-chloro-2-oxoheptanoate, benzyl 7-bromo-2-oxoheptanoate, benzyl 6-methyl-2-oxoheptanoate, benzyl 2-oxo-7-phenylheptanoate, benzyl 2-oxo-7-phenoxyheptanoate, benzyl 7-(4-t-butylphenoxy)-2-oxoheptanoate, benzyl 2-oxooctanoate, benzyl 7-methyl-2-oxooctanoate, benzyl 2-oxo-8-phenyloctanoate, benzyl 2-oxononanoate, benzyl 8-methyl-2-oxononanoate, benzyl 2-oxodecanoate, benzyl 2-oxo-10-phenoxydecanoate, benzyl 3-methyl-2-oxo-3-butenoate, benzyl 2-oxo-4-phenyl-3-butenoate, benzyl 2-oxo-4-pentenoate, benzyl 4-chloro-2-oxo-4-pentenoate, benzyl 4-methyl-2-oxo-4-pentenoate, benzyl 2-oxo-4-hexenoate, benzyl 5-methyl-2-oxo-4-hexenoate, t-butyl 2-oxo-4-phenyl-3-butynoate, 2-oxo-3-pentynoate, benzyl 2-oxo-4-hexynoate, benzyl 2-oxo-3-hexynoate, benzyl 6-methoxy-2-oxo-3-hexynoate, benzyl 7-ethoxy-2-oxo-3-heptynoate, benzyl 2-cyclopropyl-2-oxoethanoate, benzyl 2-cyclobutyl-2-oxoethanoate, benzyl 2-cyclopentyl-2-oxoethanoate, benzyl 2-cyclohexyl-2-oxoethanoate, benzyl 2-cycloheptyl-2-oxoethanoate, benzyl 2-cyclooctyl-2-oxoethanoate, benzyl 2-oxo-2-phenylethanoate, benzyl 2-(2-methylphenyl)-2-oxoethanoate, benzyl 2-(4-methoxyphenyl)-2-oxoethanoate, benzyl 2-(1-naphthyl)-2-oxoethanoate, benzyl 2-(2-naphthyl)-2-oxoethanoate, benzyl 2-(2-furyl)-2-oxoethanoate, benzyl 2-(2-benzo[b]furyl)-2-oxoethanoate, benzyl 2-oxo-2-(2-pyrrolyl)ethanoate, benzyl 2-(3-indolyl)-2-oxoethanoate, benzyl 2-oxo-2-(2-thienyl)ethanoate, benzyl 2-(2-benzo[b]thienyl)-2-oxoethanoate, benzyl 3-(benzothiazol-2-yl)-2-oxopropanoate, propyl 2-oxo-4-phenylbutanoate, butyl 2-oxo-4-phenylbutanoate, isobutyl 2-oxo-4-phenylbutanoate, sec-butyl 2-oxo-4-phenylbutanoate, t-butyl 2-oxo-4-phenylbutanoate, pentyl 2-oxo-4-phenylbutanoate, neopentyl 2-oxo-4-phenylbutanoate, hexyl 2-oxo-4-phenylbutanoate, p-nitrobenzyl 2-oxo-4-phenylbutanoate, 2-phenylethyl 2-oxo-4-phenylbutanoate, t-butyl 4-(2-nitrophenyl)-2-oxobutanoate, dimethyl 1-oxopropane-1,3-dicarboxylate, diethyl 1-oxopropane-1,3-dicarboxylate, dibutyl 1-oxopropane-1,3-dicarboxylate, methyl 2,4-dioxo-4-phenylbutanoate, ethyl 2,4-dioxo-4-(2-thienyl)butanoate, methyl 2,4-dioxopentanoate, ethyl 2,4-dioxopentanoate, methyl 2,4-dioxo-5-phenylpentanoate, methyl 5,5-dimethyl-2,4-dioxohexanoate, ethyl 2,4-dioxo-6-phenyl-5-hexenoate, and butyl 2,4-dioxo-6-phenyl-5-hexenoate.

The bisulfite which can be used in the present invention may include ammonium hydrogensulfite, sodium hydrogensulfite, and potassium hydrogensulfite. The bisulfite may be a commercially available reagent or may be prepared by the absorption of sulfur dioxide gas into ammonia water or an aqueous solution of the corresponding alkali metal hydroxide.

The amount of bisulfite to be used is usually in the range of 0.3 to 10 times greater moles, preferably 0.5 to 5 times greater moles, relative to 1 mole of pyruvic acid compound (I).

The commercially available bisulfite may sometimes be a mixture of a bisulfite and a pyrosulfite. When such a mixture is used, it may be used in terms of the net mole amount of sulfurous acid contained in the mixture.

The net amount of sulfurous acid to be used when such a mixture is used is usually in the range of 0.3 to 10 times greater moles, preferably 0.5 to 5 times greater moles, relative to the pyruvic acid compound (I).

The method of the present invention is usually carried out by the use of water as a solvent. The amount of water to be used is usually in the range of 0.5 to 50 times greater by weight, preferably 1 to 30 times greater by weight, relative to the bisulfite. The use of an organic solvent is not particularly required; however, for achieving simpler and easier treatment after the reaction, water-insoluble or slightly-soluble organic solvents may be used in admixture with water.

The organic solvent is not particularly limited, so long as it is substantially inert to the reaction; and it may include, for example, aromatic hydrocarbons such as benzene, toluene, and xylene; aliphatic hydrocarbons such as hexane, cyclohexane, and heptane; halogenated hydrocarbons such as chlorobenzene, dichlorobenzene, chloroform, and 1,2-dichlroroethane; ethers such as diethyl ether and diisopropyl ether; and ketones.

These solvents can be used each solely or in admixture of two or more kinds of solvents, and the amount of solvent to be used is usually in the range of 0.2 to 50 times greater by weight, preferably 0.5 to 30 times greater by weight, relative to the pyruvic acid compound (I).

The reaction of pyruvic acid compound (I) with bisulfite (II) in the present invention is carried out, for example, by supplying the pyruvic acid compound (I) dissolved in an organic solvent to an aqueous solution of the bisulfite. Alternatively, an aqueous solution of the bisulfite may also be supplied to the pyruvic acid compound (I) dissolved in an organic solvent. The reaction temperature is usually in the range of –5° C. to 100° C., preferably 0° C. to 80° C.

In the reaction, the pH of the reaction mixture can be controlled, if necessary. The pH controlling agent may include, for example, inorganic acids such as hydrochloric acid and sulfuric acid; organic acids such as oxalic acid, citric acid, and acetic acid; and inorganic bases such as sodium hydroxide and potassium hydroxide. The pH of the reaction mixture is preferably controlled in the range of 3 to 7, more preferably 3 to 6, by the addition of such a pH controlling agent.

The pH control is carried out, for example, by the addition of a pH controlling agent after an aqueous solution of the bisulfite is supplied to the pyruvic acid compound (I) dissolved in an organic solvent. Alternatively, the pyruvic acid compound (I) dissolved in an organic solvent may also be supplied to an aqueous solution of the bisulfite after a pH controlling agent is added to the aqueous solution of the bisulfite.

If necessary, phase transfer catalysts can be used. The phase transfer catalyst may include quaternary ammonium salts such as benzyltrimethylammonium chloride, benzyltriethylammonium chloride, tetrabutylammonium bromide, and tetrabutylammonium hydrogensulfate; and quaternary phosphonium salts such as triphenylphosphonium bromide and triphenylphosphonium iodide. The amount of phase transfer catalyst to be used is usually in the range of 0.005 to 0.8 time greater moles, preferably 0.01 to 0.2 time greater moles, relative to the pyruvic acid compound (I).

Thus, a bisulfite adduct of the pyruvic acid compound of general formula (I) can be obtained, and the bisulfite adduct may include, for example, those of the above-described pyruvic acid compound with ammonium hydrogensulfite, sodium hydrogensulfite or potassium hydrogensulfite.

The bisulfite adduct of the pyruvic acid compound (I) is obtained, for example, in the water layer by the phase separation of the reaction mixture after the reaction. In the phase separation, hydrophobic solvents or water may suitably be added, if necessary, before the phase separation, depending on the amount of water to be used in the reaction or the amount of organic solvent to be used in the reaction.

The hydrophobic solvent may include, for example, aromatic solvents such as benzene, toluene, and xylene; aliphatic solvents such as hexane, cyclohexane, and heptane; halogenated hydrocarbons such as chlorobenzene, dichlorobenzene, chloroform, and 1,2-dichloroethane; ketones such as methyl isobutyl ketone; and ethers such as diethyl ether and diisopropyl ether. The water layer can further be washed with a hydrophobic solvent to remove impurities with high efficiency.

From the water layer, the bisulfite adduct can easily be isolated, for example, by a technique such as solvent evaporation, and it can further be purified by a technique such as recrystallization.

By these procedures, organic compounds, which are contained in the pyruvic acid compound, but not reacted with the bisulfite to form an adduct, can be removed as impurities into the organic layer with high efficiency, so long as they are not mixed with water in any ratio.

After the reaction of the pyruvic acid compound (I) with the bisulfite, some portions of the pyruvic acid compound (I), if remaining unreacted, are recovered into the organic layer, and the unreacted portions of the pyruvic acid compound (I) in the organic layer can be reused in the step of reaction with an additional bisulfite. The bisulfite adduct specifically obtained may include those of the specific pyruvic acid compound as described above.

The subsequent decomposition of the bisulfite adduct of the pyruvic acid compound (I) with an acid can lead to the purification of the pyruvic acid compound (I).

As the acid, there is usually used an inorganic acid such as hydrochloric acid, sulfuric acid, or hydrobromic acid. The amount of acid to be used is usually in the range of 0.3 to 10 times greater moles, preferably 0.5 to 5 times greater moles, relative to the bisulfite adduct of the pyruvic acid compound (I).

The above decomposition is usually carried out by the use of water as a solvent. The amount of water to be used is usually in the range of 0.2 to 50 times greater by weight, preferably 0.5 to 30 times greater by weight, relative to the bisulfite adduct of the pyruvic acid compound (I).

The use of an organic solvent is not particularly required in the decomposition; however, for achieving simpler and easier treatment after the reaction, water-insoluble or slightly-soluble organic solvents can be used in admixture with water. The organic solvent is not particularly limited, so long as it is substantially inert to the reaction; and it may include, for example, aromatic hydrocarbons such as benzene, toluene, and xylene; aliphatic hydrocarbons such as hexane, cyclohexane, and heptane; halogenated hydrocarbons such as chlorobenzene, dichlorobenzene, chloroform, and 1,2-dichlroroethane; ethers such as diethyl ether and diisopropyl ether; and ketones such as methyl isobutyl ketone.

These solvents can be used each solely or in admixture of two or more kinds of solvents, and the amount of solvent to be used is usually in the range of 0.2 to 50 times greater by weight, preferably 0.5 to 30 times greater by weight, relative to the pyruvic acid compound (I).

The decomposition with an acid is carried out, for example, by the addition of the acid to an aqueous solution of the bisulfite adduct of the pyruvic acid compound. The reaction temperature is usually 0° C. to 100° C., preferably 10° C. to 80° C.

The decomposition with an acid causes the evolution of sulfur dioxide gas, and the sulfur dioxide gas can be recovered as an aqueous solution of the bisulfite by the absorption into ammonia water or an aqueous solution of an alkali metal hydroxide. The recovered aqueous solution can be reused, if necessary, in the method of the present invention.

Thus, purified portions of the pyruvic acid compound (I) are produced, and the pyruvic acid compound (1) can easily be isolated, for example, from the organic layer after the phase separation of the reaction mixture, by an ordinary technique such as concentration under reduced pressure. In the phase separation, hydrophobic solvents or water may suitably be added, if necessary, before the phase separation, depending on the amount of water to be used in the reaction or the amount of organic solvent to be used in the reaction.

The hydrophobic solvent may include, for example, aromatic solvents such as benzene, toluene, and xylene; aliphatic solvents such as hexane, cyclohexane, and heptane; halogenated hydrocarbons such as chlorobenzene, dichlorobenzene, chloroform, and 1,2-dichloroethane; ketones such as methyl isobutyl ketone; and ethers such as diethyl ether and diisopropyl ether.

Specific examples of the pyruvic acid compound (I) thus obtained may include, as a matter of course, the same compounds as described above.

The pyruvic acid compound (I), which serves as the starting material in the present invention, can easily be produced, for example, from the corresponding organic metal compound in accordance with scheme 1 or from the corresponding halide in accordance with scheme 2.

Furthermore, the pyruvic acid compound (I) can also be produced, for example, in accordance with: (1) the process in which benzaldehyde and sodium pyruvate are condensed together to give benzalpyruvic acid, and the benzalpyruvic acid is then reacted with ethyl chloroformate to give ethyl benzalpyruvate, and the ethyl benzalpyruvate is then reduced [EP387058]; or (2) the process in which phenetyl bromide is reacted with carbon monoxide in the presence of a cobalt carbonyl catalyst [J. Mol. Cat., 88, 295(1994)]. The process for producing the pyruvic acid compound (I) as the starting material is not limited to these processes, either of which can be used as the production process for the starting material in the present invention.

In these pyruvic acid compounds, when $R^1$ is $R^3(CH_2)_2$—, the pyruvic acid compound of general formula (VIII) can be obtained by reacting an alkane compound of general formula (III):

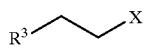
(III)

wherein $R^3$ is an optionally substituted lower alkyl group or an optionally substituted aryl group, and X is a halogen atom or a sulfonyloxy group, with a β-keto ester compound of general formula (IV):

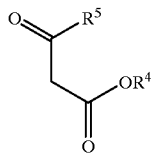
(IV)

wherein $R^4$ is an optionally substituted lower alkyl group, and $R^5$ is an optionally substituted lower alkyl group or an optionally substituted lower alkoxy group, in the presence of a base, to give a diketo compound of general formula (V):

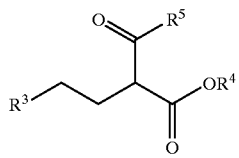
(V)

wherein $R^3$, $R^4$, and $R^5$ are as defined above; reacting the diketo compound of the general formula (V) with a nitrous acid compound of general formula (VI):

(VI)

wherein Y is a hydroxyl group, a lower alkoxy group, a halogen atom, or a —$OSO_3H$ group, to give an α-oximino ester compound of general formula (VII):

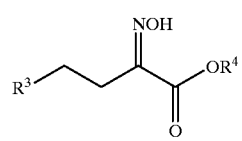
(VII)

wherein $R^3$ and $R^4$ are as defined above; reacting the α-oximino ester compound of general formula (VII) with an aldehyde compound in the presence of an acid to give a crude product of the pyruvic acid compound of general formula (VIII):

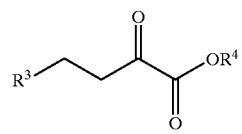
(VIII)

wherein $R^3$ and $R^4$ are as defined above; reacting the crude product with a bisulfite of general formula (II):

$MHSO_3$ (II)

wherein M is $NH_4$ or an alkali metal, to give a bisulfate adduct of the pyruvic acid compound; and decomposing the adduct with an acid.

In the alkane compound of general formula (III), the optionally substituted lower alkyl group in the substituent $R^3$ may include, for example, straight-chain or branched $C_1$–$C_6$ alkyl groups such as methyl, ethyl, n-propyl, isopropyl, n-butyl, isobutyl, sec-butyl, t-butyl, n-pentyl, neopentyl, and n-hexyl groups.

These lower alkyl groups may optionally be substituted with one to four substituents selected from halogen atoms, lower alkoxy, optionally substituted aryloxy, optionally substituted cycloalkyl, optionally substituted aryl, or optionally substituted heterocyclic groups.

These aryloxy, cycloalkyl, aryl, and heterocyclic groups may further be substituted with one to three substituents selected from halogen atoms, nitro, trifluoromethyl, lower alkyl or lower alkoxy groups. The lower alkyl group as used herein may include, for example, straight-chain or branched $C_1$–$C_6$ alkyl groups such as methyl, ethyl, n-propyl, isopropyl, n-butyl, isobutyl, sec-butyl, t-butyl, n-pentyl, neopentyl, an n-hexylm groups. The lower alkoxy group as used herein may include, for example, straight-chain or branched $C_1$–$C_6$ alkoxy groups such as methoxy, ethoxy, n-propoxy, isopropoxy, n-butoxy, isobutoxy, sec-butoxy, t-butoxy, n-pentyloxy, neopentyloxy, and n-hexyloxy groups.

The optionally substituted aryl group in the substituent $R^3$ may include, for example, phenyl and naphthyl groups. These aryl groups may optionally be substituted with one to three substituents selected from halogen atoms, nitro, trifluoromethyl, lower alkyl, or lower alkoxy groups. The lower alkyl group as used herein may include, for example, the same straight-chain or branched $C_1$–$C_6$ alkyl groups as described above. The lower alkoxy group as used herein may include, for example, the same straight-chain or branched $C_1$–$C_6$ alkoxy groups as described above.

The substituent X in the general formula (III) may include, for example, halogen atoms such as chlorine, bromine, and iodine atoms; and sulfonyloxy groups such as methanesulfonyloxy, trifluoromethanesulfonyloxy, benzenesulfonyloxy, and p-toluenesulfonyloxy groups.

The alkane compound may include, for example, 1-bromopropane, 1-cyclohexyl-3-bromopropane, 1-bromo-3-phenylpropane, 1-chloro-3-(4-chlorophenyl)propane, 1-bromo-3-(3-methoxyphenyl)propane, 1-bromo-3-(4-methoxyphenyl)propane, 1-bromo-3,3-diphenylpropane, 1-chloro-3-methoxy-3-phenylpropane, 1-chloro-3-(4-chlorophenyl)-3-methoxypropane, 1-chloro-3-isopropoxy-3-phenylpropane, 1-chloro-3-isopropoxy-3-(4-methylphenyl)propane, 1-bromo-3-phenoxypropane, 1-chloro-3-(4-fluorophenoxy)propane, 1-bromo-3-(2-bromo-4-methylphenoxy)propane, 1-bromo-3-(2,6-dibromo-4-methylphenoxy)propane, 1-bromobutane, 1-bromo-3-methylbutane, 1-bromo-3,3-dimethylbutane, 1-chloro-3-phenylbutane, 1-bromo-4-phenylbutane, 1-bromo-4-phenoxybutane, 1-chloro-4-(2-methylphenoxy)butane, 1-chloro-4-(3-methylphenoxy)butane, 1-chloro-4-(4-methylphenoxy)butane, 1-iodo-4-(4-nitrophenoxy)butane, 1-bromo-4-(2,5-dimethylphenoxy)butane, 1-bromopentane, 1,5-dichloropentane, 1-bromo-5-chloropentane, 1-chloro-5-iodopentane, 1,5-bromopentane, 1-bromo-5-iodopentane, 5-chloropentyl methanesulfonate, 5-chloropentyl p-toluenesulfonate, 1-bromo-4-methylpentane, 1-chloro-5-phenylpentane, 1-chloro-5-phenoxypentane, 1-bromo-5-(4-t-butylphenoxy)pentane, 1-bromohexane, 1-bromo-5-methylhexane, 1-bromo-6-phenylhexane, 1-bromoheptane, 1-bromo-6-methylheptane, 1-chlorooctane, 1-bromooctane, 1-iodooctane, octyl methanesulfonate, octyl trifluoromethanesulfonate, octyl benzenesulfonate, octyl p-toluenesulfonate, 1-bromo-8-phenoxyoctane, (2-chloroethyl)benzene, (2-bromoethyl)benzene, (2-iodoethyl)benzene, 2-phenylethyl methanesulfonate, 2-phenylethyl trifluoromethanesulfoante, 2-phenylethyl benzenesulfonate, 2-phenylethyl p-toluenesulfonate, 1-chloro-2-(4-fluorophenyl)ethane, 1-chloro-2-(3-chlorophenyl)ethane, 1-chloro-2-(4-chlorophenyl)ethane, 1-bromo-2-(2-bromophenyl)ethane, 1-chloro-2-(2-nitrophenyl)ethane, 1-bromo-2-(2-nitrophenyl)ethane, 1-bromo-2-(4-nitrophenyl)ethane, 1-chloro-2-(4-chloro-2-nitrophenyl)ethane, 1-bromo-2-(4-chloro-2-nitrophenyl)ethane, 1-(4-bromo-2-nitrophenyl)-2-chloroethane, 1-bromo-2-(4-bromo-2-nitrophenyl)ethane, 1-bromo-2-(3-trifluoromethylphenyl)ethane, 1-bromo-2-(2-methylphenyl)ethane, 1-bromo-2-(2,4-dimethylphenyl)ethane, 1-chloro-2-(2-methoxyphenyl)ethane, 1-bromo-2-(4-methoxyphenyl)ethane, 1-chloro-2-(2,5-dimethoxyphenyl)ethane, 1-(3,4-dimethoxyphenyl)-2-iodoethane, 1-bromo-2-(1-naphthyl)ethane, 1-bromo-2-(2-nitro-1-naphthyl)ethane, 1-bromo-2-(2-naphthyl)ethane, 1-bromo-2-(1-chloro-2-naphthyl)ethane, and 1-bromo-2-(1-bromo-2-naphthyl)ethane, 1-bromo-2-(1-nitro-2-naphthyl)ethane.

The alkane compound (I) can easily be synthesized from the corresponding alcohol, for example, in accordance with J. Am. Chem. Soc., 55, 4652(1933) or J. Med. Chem., 26, 947(1983), or from the corresponding carboxylic acid, for example, in accordance with J. Med. Chem., 20, 1020 (1977).

In the β-keto ester compound of general formula (IV), the optionally substituted lower alkyl group represented by substituent $R^4$ may include, for example, straight-chain or branched $C_1$–$C_6$ alkyl groups such as methyl, ethyl, n-propyl, isopropyl, n-butyl, isobutyl, sec-butyl, t-butyl, n-pentyl, neopentyl, and n-hexyl groups. These alkyl groups may optionally be substituted with one to two optionally substituted aryl groups. The aryl group as used herein may include, for example, phenyl and p-nitrophenyl groups. The lower alkyl group substituted with the aryl group may include, for example, benzyl, p-nitrobenzyl, and 2-phenylethyl groups.

The lower alkyl group represented by substituent $R^5$ in the general formula (IV) may include, for example, straight-chain or branched $C_1$–$C_6$ alkyl groups such as methyl, ethyl, n-propyl, isopropyl, n-butyl, isobutyl, sec-butyl, t-butyl, n-pentyl, neopentyl, and n-hexyl groups.

The lower alkoxy group represented by substituent $R^5$ may include, for example, straight-chain or branched $C_1$–$C_6$ alkoxy groups such as methoxy, ethoxy, n-propoxy, isopropoxy, n-butoxy, isobutoxy, sec-butoxy, t-butoxy, n-pentyloxy, neopentyloxy, and n-hexyloxy.

When the substituent $R^5$ is a lower alkoxy group or is represented by —$OR^6$, $R^6$ is preferably the same lower alkyl group as the lower alkyl group represented by $R^4$.

The β-keto ester compound may include, for example, methyl 3-oxobutanoate, ethyl 3-oxobutanoate, propyl 3-oxobutanoate, isopropyl 3-oxobutanoate, butyl 3-oxobutanoate, isobutyl 3-oxobutanoate, sec-butyl 3-oxobutanoate, t-butyl 3-oxobutanoate, pentyl 3-oxobutanoate, neopentyl 3-oxobutanoate, hexyl 3-oxobutanoate, benzyl 3-oxobutanoate, p-nitrobenzyl 3-oxobutanoate, 2-phenylethyl 3-oxobutanoate, methyl 3-oxopentanoate, ethyl 3-oxopentanoate, methyl 4-methyl-3-oxopentanoate, ethyl 4-methyl-3-oxopentanoate, methyl 4,4-dimethyl-3-oxopentanoate, ethyl 4,4-dimethyl-3-oxopentanoate, methyl 3-oxohexanoate, ethyl 3-oxohexanoate, ethyl 5-methyl-3-oxohexanoate, ethyl 3-oxoheptanoate, methyl 3-oxooctanoate, methyl 3-oxononanoate, dimethyl malonate, diethyl malonate, dipropyl malonate, diisopropyl malonate, dibutyl malonate, and di-t-butyl malonate. The amount of β-keto ester compound to be used is usually in the range of 0.01 to 10 times greater moles, preferably 0.1 to 5 times greater moles, relative to the alkane compound.

The reaction is usually carried out in the presence of a base. The base may include, for example, alkali metal hydroxides such as sodium hydroxide and potassium hydroxide; alkali metal carbonates such as sodium carbonate and potassium carbonate; alkali metal alkoxides such as sodium methoxide, sodium ethoxide, and potassium, t-butoxide; and hydroxides of alkali metals or alkaline earth metals, such as sodium hydroxide and calcium hydroxide. Preferably used is potassium carbonate. These bases are used each solely or in admixture of two or more kinds of bases, and the amount of base to be used is usually in the range of 0.8 to 20 times greater moles, preferably 0.9 to 10 times greater moles, relative to smaller one of the mole amounts of alkane compound (III) or β-keto ester compound (IV) to be used.

The reaction may be carried out without solvent or may also be carried out by the use of a solvent. The solvent is not particularly limited, so long as it is substantially inert to the reaction; and it may include, for example, aromatic hydrocarbons such as benzene, toluene, and xylene; aliphatic hydrocarbons such as hexane, cyclohexane, and heptane; halo-genated hydrocarbons such as chlorobenzene, dichlorobenzene, chloroform, and 1,2-dichloroethane; ethers such as diethyl ether and diisopropyl ether; ketones such as methyl isobutyl ketone; alcohols such as methanol, ethanol, and 2-propanol; amides such as N,N-dimethylformamide and N-methyl-2-pyrrolidone; sulfoxides such as dimethyl sulfoxide; and nitrites such as acetonitrile.

When solvents are used, these solvents are used each solely or in admixture of two or more kinds of solvents, and the amount of solvent to be used is usually at most 50 times greater by weight, relative to the alkane compound (III).

When potassium carbonate is used as a base, it is preferred from the viewpoint of yield to control the total water content in the reaction system. The total water content in the reaction system is preferably controlled by the addition of water, if necessary, during the reaction so that it usually comes to 0.005 to 0.08 time greater by weight, preferably 0.005 to 0.05 time greater by weight, relative to the pure content of the potassium carbonate. When the potassium carbonate contains a small amount of water, the water content is preferably controlled, if necessary, so that it comes within the above range, taking into consideration the amount of water contained in the potassium carbonate.

In the reaction, phase transfer catalysts can be used, if necessary. The phase transfer catalyst may include, for example, quaternary ammonium salts such as benzyltrimethylammonium chloride, benzyltriethylammonium chloride, tetrabutylammonium bromide, and tetrabutylammonium hydrogensulfate; and quaternary phosphonium salts such as triphenylphosphonium bromide and triphenylphosphonium iodide. The amount of phase transfer catalyst to be used is usually in the range of 0.005 to 0.8 time greater moles, preferably 0.01 to 0.2 time greater moles, relative to the alkane compound (III).

The reaction is carried out, for example, by supplying a base into a mixture of alkane compound (III), β-keto ester compound (IV), and a solvent. Alternatively, the β-keto ester compound (IV) may also be supplied into a mixture of the alkane compound (III), the base, and the solvent; or the alkane compound (III) may also be supplied into a mixture of the β-keto ester compound (IV), the base, and the solvent.

When potassium carbonate is used as a base, the reaction is carried out, for example, by supplying potassium carbonate into a mixture of alkane compound (III), β-keto ester compound (IV), a solvent, and water. Alternatively, the β-keto ester compound (IV) may also be supplied into a mixture of the alkane compound (III), potassium carbonate, the solvent, and water; or the alkane compound (III) may also be supplied into a mixture of the β-keto ester compound (IV), potassium carbonate, the solvent, and water. Alternatively, the alkane compound (III), β-ketoester compound (IV), potassium carbonate, and water have been all previously mixed, and the mixture may be controlled to a desired reaction temperature.

The reaction temperature is usually in the range of $-50°$ C. to $300°$ C., preferably $0°$ C. to $150°$ C.

Thus, diketo compound (V) is produced, and the diketo compound (V) may be obtained in the organic layer, for example, by filtering the reaction mixture to give a filtrate, washing the filtered solid with a hydrophobic solvent to give a wash, and combining the filtrate and the wash into the organic layer. The hydrophobic solvent to be used for washing the filtered solid may include, for example, aromatic hydrocarbons such as benzene, toluene, and xylene; aliphatic hydrocarbons such as hexane, cyclohexane, and heptane; halogenated hydrocarbons such as chlorobenzene, dichlorobenzene, chloroform, and 1,2-dichloroethane; ketones such as methyl isobutyl ketone; and ethers such as diethyl ether and diisopropyl ether. The filtration of the reaction mixture may be carried out after a hydrophobic solvent is suitably added depending on the amount of solvent to be used in the reaction. The hydrophobic solvent may include, for example, the same hydrophobic solvents as described above.

Alternatively, the organic layer can also be obtained, for example, by the addition of water to the reaction mixture to dissolve the solid and the subsequent phase separation of the mixture. When the amount of organic solvent to be used in the reaction is small, it may sometimes be difficult to easily achieve the phase separation, in which case, however, the addition of a suitable hydrophobic solvent may suitably be followed by the phase separation. The hydrophobic solvent may include, for example, aromatic hydrocarbons such as benzene, toluene, and xylene; aliphatic hydrocarbons such as hexane, cyclohexane, and heptane; halogenated hydrocarbons such as chlorobenzene, dichlorobenzene, chloroform, and 1,2-dichloroethane; ketones such as methyl isobutyl ketone; and ethers such as diethyl ether and diisopropyl ether.

Thus, the diketo compound (V) containing organic layer is obtained. The diketo compound (V) can easily be isolated from the orgaLnic layer, for example, by a technique such as solvent evaporation, and it can be used in the next step without purification. Alternatively, the diketo compound (V) containing organic layer can also be used as such a solution in the next step without concentration.

Thus, the diketo compound of general formula (V) is obtained. The diketo compound may include, for example, methyl 3-oxo-2-(2-phenylethyl)butanoate, methyl 2-[(4-fluorophenyl)ethyl]-3-oxobutanoate, methyl 2-[(3-chlorophenyl)ethyl]-3-oxobutanoate, methyl 2-[(4-chlorophenyl)ethyl]-3-oxobutanoate, methyl 2-[(2-bromophenyl)ethyl]-3-oxobutanoate, methyl 2-[(2-nitrophenyl)ethyl]-3-oxobutanoate, methyl 2-[(4-nitrophenyl)ethyl]-3-oxobutanoate, methyl 2-[(4-chloro-2-nitrophenyl)ethyl]-3-oxobutanoate, methyl 2-[(4-bromo-2-nitrophenyl)ethyl]-3-oxobutanoate, methyl 3-oxo-2-[(3-trifluoromethylphenyl)ethyl]butanoate, methyl 2-[(2-methylphenyl)ethyl]-3-oxobutanoate, methyl 2-[(2,4-dimethylphenyl)ethyl]-3-oxobutanoate, methyl 2-[(2-methoxyphenyl)ethyl]-3-oxobutanoate, methyl 2-[(4-methoxyphenyl)ethyl]-3-oxobutanoate, methyl 2-[(2,5-dimethoxyphenyl)ethyl]-3-oxobutanoate, methyl 2-[(3,4-dimethoxyphenyl)ethyl]-3-oxobutanoate, methyl 2-[(1-naphthyl)ethyl]-3-oxobutanoate, methyl 2-[(2-nitro-1-naphthyl)ethyl]-3-oxobutanoate, methyl 2-[(2-naphthyl)ethyl]-3-oxobutanoate, methyl 2-[(1-chloro-2-naphthyl)ethyl]-3-oxobutanoate, methyl 2-[(1-bromo-2-naphthyl)ethyl]-3-oxobutanoate, methyl 2-[(1-nitro-2-naphthyl)ethyl]-3-oxobutanoate, methyl 2-(1-oxoethyl)pentanoate, methyl5-cyclohexyl-2-(1-oxoethyl)pentanoate, methyl 2-(1-oxoethyl)-5-phenylpentanoate, methyl 5-(3-chlorophenyl)-2-(1-oxoethyl)pentanoate, methyl 5-(3-methoxyphenyl)-2-(1-oxoethyl)pentanoate, methyl 5-(4-methoxyphenyl)-2-(1-oxoethyl)pentanoate, methyl 5,5-diphenyl-2-(1-oxoethyl)pentanoate, methyl 5-methoxy-2-(1-oxoethyl)-5-phenylpentanoate, methyl 5-(4-chlorophenyl)-5-methoxy-2-(1-oxoethyl)pentanoate, methyl 5-isopropoxy-2-(1-oxoethyl)-5-phenylpentanoate, methyl 5-isopropoxy-5-(4-methylphenyl)-2-(1-oxoethyl)pentanoate, methyl 2-(1-oxoethyl)-5-phenoxypentanoate, methyl 5-(4-fluorophenoxy)-2-(1-oxoethyl)pentanoate, methyl 5-(2-bromo-4-methylphenoxy)-2-(1-oxoethyl)pentanoate, methyl 5-(2,6-dibromo-4-methylphenoxy)-2-(1-oxoethyl) pentanoate, methyl 2-(1-oxoethyl)hexanoate, methyl 5-methyl-2-(1-oxoethyl)hexanoate, methyl 5,5-dimethyl-2-(1-oxoethyl)hexanoate, methyl 2-(1-oxoethyl)-5-phenylhexanoate, methyl 2-(1-oxoethyl)-6-phenylhexanoate, methyl 2-(1-oxoethyl)-6-phenoxyhexanoate, methyl 6-(2-methylphenoxy)-2-(1-oxoethyl)hexanoate, methyl 6-(3-methylphenoxy)-2-(1-oxoethyl)hexanoate, methyl 6-(4-methylphenoxy)-2-(1-oxoethyl)hexanoate, methyl 6-(4-nitrophenoxy)-2-(1- oxoethyl)hexanoate, methyl 6-(2,5-dimethylphenoxy)-2-(1-oxoethyl)hexanoate, methyl 2-(1-oxoethyl)heptanoate, methyl 7-chloro-2-(1-oxoethyl)heptanoate, methyl 7-bromo-2-(1-oxoethyl)heptanoate, methyl 6-methyl-2-(1-oxoethyl)heptanoate, methyl 2-(1-oxoethyl)-7-phenylheptanoate, methyl 2-(1-oxoethyl)-7-phenoxyheptanoate, methyl 7-(4-t-butylphenoxy)-2-(1-oxoethyl)heptanoate, methyl 2-(1-oxoethyl)octanoate, methyl 7-methyl-2-(1-oxoethyl)octanoate, methyl 2-(1-oxoethyl)-8-phenyloctanoate, methyl 2-(1-oxoethyl) nonanoate, methyl 8-methyl-2-(1-oxoethyl)nonanoate, methyl 2-(1-oxoethyl)decanoate, methyl 2-(1-oxoethyl)-10-phenoxydecanoate, ethyl 3-oxo-2-(2-phenylethyl)butanoate, ethyl 2-[(4-fluorophenyl)ethyl]-3-oxobutanoate, ethyl 2-[(3-chlorophenyl)ethyl]-3-oxobutanoate, ethyl 2-[(4-chlorophenyl)ethyl]-3-oxobutanoate, ethyl 2-[(2-bromophenyl)ethyl]-3-oxobutanoate, ethyl 2-[(2-nitrophenyl)ethyl]-3-oxobutanoate, ethyl 2-[(4-nitrophenyl)ethyl]-3-oxobutanoate, ethyl 2-[(4-chloro-2-nitrophenyl)ethyl]-3-oxobutanoate, ethyl 2-[(4-bromo-2-nitrophenyl)ethyl]-3-oxobutanoate, ethyl 3-oxo-2-[(3-trifluoromethylphenyl)ethyl]butanoate, ethyl 2-[(2-methylphenyl)ethyl]-3-oxobutanoate, ethyl 2-[(2,4-dimethylphenyl)ethyl]-3-oxobutanoate, ethyl 2-[(2-methoxyphenyl)ethyl]-3-oxobutanoate, ethyl 2-[(4-methoxyphenyl)ethyl]-3-oxobutanoate, ethyl 2-[(2,5-dimethoxyphenyl)ethyl]-3-oxobutanoate, ethyl 2-[(3,4-dimethoxyphenyl)ethyl]-3-oxobutanoate, ethyl 2-[(1-naphthyl)ethyl]-3-oxobutanoate, ethyl 2-[(2-nitro-1-naphthyl)ethyl]-3-oxobutanoate, ethyl 2-[(2phehyl)ethyl]-3-oxobutanoate, ethyl 2-[(1-chloro-2-naphthyl)ethyl]-3-oxobutanoate, -napthyl 2-[(1-bromo-2-naphthyl)ethyl]-3-oxobutanoate, ethyl 2-[(1-nitro-2-naphthyl)ethyl]-3-oxobutanoate, ethyl 2-(1-oxoethyl)pentanoate, ethyl 5-cyclohexyl-2-(1-oxoethyl)pentanoate, ethyl 2-(1-oxoethyl)-5-phenylpentanoate, ethyl 5-(3-chlorophenyl)-2-(1-oxoethyl)pentanoate, ethyl 5-(3-methoxyphenyl)-2-(1-oxoethyl)pentanoate, ethyl 5-(4-methoxyphenyl)-2-(1-oxoethyl)pentanoate, ethyl 5,5-diphenyl-2-(1-oxoethyl)pentanoate, ethyl 5-methoxy-2-(1-oxoethyl)-5-phenylpentanoate, ethyl 5-(4-chlorophenyl)-5-methoxy-2-(1-oxoethyl)pentanoate, ethyl 5-isopropoxy-2-(1-oxoethyl)-5-phenylpentanoate, ethyl 5-isopropoxy-5-(4-methylphenyl)-2-(1-oxoethyl)pentanoate, ethyl 2-(1-oxoethyl)-5-phenoxypentanoate, ethyl 5-(4-fluorophenoxy)-2-(1-oxoethyl)pentanoate, ethyl 5-(2-bromo-4-methylphenoxy)-2-(1-oxoethyl)pentanoate, ethyl 5-(2,6-dibromo-4-methylphenoxy)-2-(1-oxoethyl)pentanoate, ethyl 2-(1-oxoethyl)hexanoate, ethyl 5-methyl-2-(1-oxoethyl)hexanoate, ethyl 5,5-dimethyl-2-(1-oxoethyl) hexanoate, ethyl 2-(1-oxoethyl)-5-phenylhexanoate, ethyl 2-(1-oxoethyl)-6-phenylhexanoate, ethyl 2-(1-oxoethyl)-6-phenoxyhexanoate, ethyl 6-(2-methylphenoxy)-2-(1-oxoethyl)hexanoate, ethyl 6-(3-methylphenoxy)-2-(1-oxoethyl)hexanoate, ethyl 6-(4-methylphenoxy)-2-(1-oxoethyl)hexanoate, ethyl 6-(4-nitrophenoxy)-2-(1-oxoethyl)hexanoate, ethyl 6-(2,5-dimethylphenoxy)-2-(1-oxoethyl)hexanoate, ethyl 2-(1-oxoethyl)heptanoate, ethyl 7-chloro-2-(1-oxoethyl)heptanoate, ethyl 7-bromo-2-(1-oxoethyl)heptanoate, ethyl 6-methyl-2-(1-oxoethyl) petanoate, ethyl 2-(1-oxoethyl)-7-phenylheptanoate, ethyl 2-(1-oxoethyl)-7-phenoxyheptanoate, ethyl 7-(4-t-butylphenoxy)-2-(1-oxoethyl)heptanoate, ethyl 2-(1-oxoethyl)octanoate, ethyl 7-methyl-2-(1-oxoethyl) octanoate, ethyl 2-(1-oxoethyl)-8-phenyloctanoate, ethyl 2-(1-oxoethyl)nonanoate, ethyl 8-methyl-2-(1-oxoethyl) nonanoate, ethyl 2-(1-oxoethyl)decanoate, ethyl 2-(1-oxoethyl)-10-phenoxydecanoate, isopropyl 3-oxo-2-(2-phenylethyl)butanoate, isopropyl 2-[(4-fluorophenyl)ethyl]-3-oxobutanoate, isopropyl 2-[(3-chlorophenyl)ethyl]-3-oxobutanoate, isopropyl 2-[(4-chlorophenyl)ethyl]-3-oxobutanoate, isopropyl 2-[(2-bromophenyl)ethyl]-3-oxobutanoate, isopropyl 2-[(2-nitrophenyl)ethyl]-3-oxobutanoate, isopropyl 2-[(4-nitrophenyl)ethyl]-3-oxobutanoate, isopropyl 2-[(4-chloro-2-nitrophenyl)ethyl]-3-oxobutanoate, isopropyl 2-[(4-bromo-2-nitrophenyl)ethyl]-3-oxobutanoate, isopropyl 3-oxo-2-[(3-trifluoromethylphenyl)ethyl]butanoate, isopropyl 2-[(2-methylphenyl)ethyl]-3-oxobutanoate, isopropyl 2-[(2,4-dimethylphenyl)ethyl]-3-oxobutanoate, isopropyl 2-[(2-methoxyphenyl)ethyl]-3-oxobutanoate, isopropyl 2-[(4-methoxyphenyl)ethyl]-3-oxobutanoate, isopropyl 2-[(2,5-dimethoxyphenyl)ethyl]-3-oxobutanoate, isopropyl 2-[(3,4-dimethoxyphenyl)ethyl]-3-oxobutanoate, isopropyl 2-[(1-naphthyl)ethyl]-3-oxobutanoate, isopropyl 2-[(2-nitro-1-naphthyl)ethyl]-3-oxobutanoate, isopropyl 2-[(2-naphthyl) ethyl]-3-oxobutanoate, isopropyl 2-[(1-chloro-2-naphthyl) ethyl]-3-oxobutanoate, isopropyl 2-[(1-bromo-2-naphthyl) ethyl]-3-oxobutanoate, isopropyl 2-[(1-nitro-2-naphthyl) ethyl]-3-oxobutanoate, isopropyl 2-(1-oxoethyl)pentanoate, isoprpyl 5-cyclohexyl-2-(1-oxoethyl)pentanoate, isopropyl 2-(1-oxoethyl)-5-phenylpentanoate, isopropyl 5-(3-chlorophenyl)-2-(1-oxoethyl)pentanoate, isopropyl 5-(3-methoxyphenyl)-2-(1-oxoethyl)pentanoate, isopropyl 5-(4-methoxyphenyl)-2-(1-oxoethyl)pentanoate, isopropyl 5,5-diphenyl-2-(1-oxoethyl)pentanoate, isopropyl 5-methoxy-2-(1-oxoethyl)-5-phenylpentanoate, isopropyl 5-(4-chlorophenyl)-5-methoxy-2-(1-oxoethyl)pentanoate, isopropyl 5-isopropoxy-2-(1-oxoethyl)-5-phenylpentanoate, isopropyl 5-isopropoxy-5-(4-methylphenyl)-2-(1-oxoethyl) pentanoate, isopropyl 2-(1-oxoethyl)-5-phenoxypentanoate, isopropyl 5-(4-fluorophenoxy)-2-(1-oxoethyl)pentanoate, isopropyl 5-(2-bromo-4-methylphenoxy)-2-(1-oxoethyl) pentanoate, isopropyl 5-(2,6-dibromo-4-methylphenoxy)-2-(1-oxoethyl)pentanoate, isopropyl 2-(1-oxoethyl)hexanoate, isopropyl 5-methyl-2-(1-oxoethyl)hexanoate, isopropyl 5,5-dimethyl-2-(1-oxoethyl)hexanoate, isopropyl 2-(1-oxoethyl)-5-phenylhexanoate, isopropyl 2-(1-oxoethyl)-6-phenylhexanoate, isopropyl 2-(1-oxoethyl)-6-phenoxyhexanoate, isopropyl 6-(2-methylphenoxy)-2-(1-oxoethyl)hexanoate, isopropyl 6-(3-methylphenoxy)-2-(1-oxoethyl)hexanoate, isopropyl 6-(4-methylphenoxy)-2-(1-oxoethyl)hexanoate, isopropyl 6-(4-nitrophenoxy)-2-(1-oxoethyl)hexanoate, isopropyl 6-(2,5-dimethylphenoxy)-2-(1-oxoethyl)hexanoate, isopropyl 2-(1-oxoethyl)heptanoate, isopropyl 7-chloro-2-(1-oxoethyl)heptanoate, isopropyl 7-bromo-2-(1-oxoethyl)heptanoate, isopropyl 6-methyl-2-(1-oxoethyl)heptanoate, isopropyl 2-(1-oxoethyl)-7-phenylheptanoate, isopropyl 2-(1-oxoethyl)-7-phenoxyheptanoate, isopropyl 7-(4-t-butylphenoxy)-2-(1-oxoethyl)heptanoate, isopropyl 2-(1-oxoethyl)octanoate, isopropyl 7-methyl-2-(1-oxoethyl)octanoate, isopropyl 2-(1-oxoethyl)-8-phenyloctanoate, isopropyl 2-(1-oxoethyl) nonanoate, isopropyl 8-methyl-2-(1-oxoethyl)nonanoate, isopropyl 2-(1-oxoethyl)decanoate, isopropyl 2-(1-oxoethyl)-10-phenoxydecanoate, 3-oxo-2-(2-phenylethyl) butanoate, benzyl 2-[(4-fluorophenyl)ethyl]-3-oxobutanoate, benzyl 2-[(3-chlorophenyl)ethyl]-3-oxobutanoate, benzyl 2-[(4-chlorophenyl)ethyl]-3-oxobutanoate, benzyl 2-[(2-bromophenyl)ethyl]-3-oxobutanoate, benzyl 2-[(2-nitrophenyl)ethyl]-3-oxobutanoate, benzyl 2-[(4-nitrophenyl)ethyl]-3-oxobutanoate, benzyl 2-[(4-chloro-2-nitrophenyl)ethyl]-3-oxobutanoate, benzyl 2-[(4-bromo-2-nitrophenyl)ethyl]-3- oxobutanoate, benzyl 3-oxo-2-[(3-trifluoromethylphenyl)ethyl]butanoate, benzyl 2-[(2-methylphenyl)ethyl]-3-oxobutanoate, benzyl 2-[(2,4-dimethylphenyl)ethyl]-3-oxobutanoate, benzyl 2-[(2-methoxyphenyl)ethyl]-3-oxobutanoate, benzyl 2-[(4-methoxyphenyl)ethyl]-3-oxobutanoate, benzyl 2-[(2,5-dimethoxyphenyl)ethyl]-3-oxobutanoate, benzyl 2-[(3,4-dimethoxyphenyl)ethyl]-3-oxobutanoate, benzyl 2-[(1-naphthyl)ethyl]-3-oxobutaonoate, benzyl 2-[(2-nitro-1-naphthyl)ethyl]-3-oxobutanoate, benzyl 2-[(2-naphthyl)ethyl]-3-oxobutanoate, benzyl 2-[(1-chloro-2-naphthyl)ethyl]-3-oxobutanoate, benzyl 2-[(1-bromo-2-naphthyl)ethyl]-3-oxobutanoate, benzyl 2-[(1-nitro-2-naphthyl)ethyl]-3-oxobutanoate, benzyl 2-(1-oxoethyl)pentanoate, benzyl 5-cyclohexyl-2-(1-oxoethyl)pentanoate, benzyl 2-(1-oxoethyl)-5-phenylpentanoate, benzyl 5-(3-chlorophenyl)-2-(1-oxoethyl)pentanoate, benzyl 5-(3-methoxyphenyl)-2-(1-oxoethyl)pentanoate, benzyl 5-(4-methoxyphenyl)-2-(1-oxoethyl)pentanoate, benzyl 5,5-diphenyl-2-(1-oxoethyl)pentanoate, benzyl 5-methoxy-2-(1-oxoethyl)-5-phenylpentanoate, benzyl 5-(4-chlorophenyl)-5-methoxy-2-(1-oxoethyl)pentanoate, benzyl 5-isopropoxy-2-(1-oxoethyl)-5-phenylpentanoate, benzyl 5-isopropoxy-5-(4-methylphenyl)-2-(1-oxoethyl)pentanoate, benzyl 2-(1-oxoethyl)-5-phenoxypentanoate, benzyl 5-(4-fluorophenoxy)-2-(1-oxoethyl)pentanoate, benzyl 5-(2-bromo-4-methylphenoxy)-2-(1-oxoethyl)pentanoate, benzyl 5-(2,6-dibromo-4-methylphenoxy)-2-(1-oxoethyl)pentanoate, benzyl 2-(1-oxoethyl)hexanoate, benzyl 5-methyl-2-(1-oxoethyl)hexanoate, benzyl 5,5-dimethyl-2-(1-oxoethyl)hexanoate, benzyl 2-(1-oxoethyl)-5-phenylhexanoate, benzyl 2-(1-oxoethyl)-6-phenylhexanoate, benzyl 2-(1-oxoethyl)-6-phenoxyhexanoate, benzyl 6-(2-methylphenoxy)-2-(1-oxoethyl)hexanoate, benzyl 6-(3-methylphenoxy)-2-(1-oxoethyl)hexanoate, benzyl 6-(4-methylphenoxy)-2-(1-oxoethyl)hexanoate, benzyl 6-(4-nitrophenoxy)-2-(1-oxoethyl)hexanoate, benzyl 6-(2,5-dimethylphenoxy)-2-(1-oxoethyl)hexanoate, benzyl 2-(1-oxoethyl)heptanoate, benzyl 7-chloro-2-(1-oxoethyl)heptanoate, benzyl 7-bromo-2-(1-oxoethyl)heptanoate, benzyl 6-methyl-2-(1-oxoethyl)heptanoate, benzyl 2-(1-oxoethyl)-7-phenylheptanoate, benzyl 2-(1-oxoethyl)-7-phenoxyheptanoate, benzyl 7-(4-t-butylphenoxy)-2-(1-oxoethyl)heptanoate, benzyl 2-(1-oxoethyl)octanoate, benzyl 7-methyl-2-(1-oxoethyl)octanoate, benzyl 2-(1-oxoethyl)-8-phenyloctanoate, benzyl 2-(1-oxoethyl)nonanoate, benzyl 8-methyl-2-(1-oxoethyl)nonanoate, benzyl 2-(1-oxoethyl)decanoate, benzyl 2-(1-oxoethyl)-10-phenoxydecanoate, propyl 3-oxo-2-(2-phenylethyl)butanoate, butyl 3-oxo-2-(2-phenylethyl)butanoate, isobutyl 3-oxo-2-(2-phenylethyl)butanoate, sec-butyl 3-oxo-2-(2-phenylethyl)butanoate, t-butyl 3-oxo-2-(2-phenylethyl)butanoate, pentyl 3-oxo-2-(2-phenylethyl)butanoate, neopentyl 3-oxo-2-(2-phenylethyl)butanoate, hexyl 3-oxo-2-(2-phenylethyl)butanoate, p-nitrobenzyl 3-oxo-2-(2-phenylethyl)butanoate, 2-phenylethyl 3-oxo-2-(2-phenylethyl)butanoate, t-butyl 3-oxo-2-[2-(2-nitrophenyl)ethyl]butanoate, methyl 3-oxo-2-(2-phenylethyl)pentanoate, ethyl 3-oxo-2-(2-phenylethyl)pentanoate, methyl 4-methyl-3-oxo-2-(2-phenylethyl)pentanoate, ethyl 4-methyl-3-oxo-2-(2-phenylethyl)pentanoate, methyl 4,4-dimethyl-3-oxo-2-(2-phenylethyl)pentanoate, ethyl 4,4-dimethyl-3-oxo-2-(2-phenylethyl)pentanoate, methyl 3-oxo-2-(2-phenylethyl)hexanoate, ethyl 3-oxo-2-(2-phenylethyl)hexanoate, ethyl 5-methyl-3-oxo-2-(2-phenylethyl)hexanoate, ethyl 3-oxo-2-(2-phenylethyl)heptanoate, methyl 3-oxo-2-(2-phenylethyl)octanoate, methyl 3-oxo-2-(2-phenylethyl)nonanoate, dimethyl 6-chlorohexane-1,1-dicarboxylate, diethyl 6-chlorohexane-1,1-dicarboxylate, dimethyl 3-phenylpropane-1,1-dicarboxylate, diethyl 3-phenylpropane-1,1-dicarboxylate, diisopropyl 3-phenylpropane-1,1-dicarboxylate, di-t-butyl 3-phenylpropane-1,1-dicarboxylate, dimethyl 3-(2-nitrophenyl)propane-1,1-dicarboxylate, diethyl 3-(2-nitrophenyl)propane-1,1-dicarboxylate, dimethyl nonane-1,1-dicarboxylate, diethyl nonane-1,1-dicarboxylate, and diisopropyl nonane-1,1-dicarboxylate.

The diketo compound (V) obtained is then reacted with a nitrous acid compound of general formula (VI) to produce an cc-oximino ester compound of general formula (VII).

The halogen atom in the substituent Y in the general formula (VI) may include, for example, chlorine and bromine atoms. The lower alkoxy group may include, for example, straight-chain or branched $C_1$–$C_6$ alkoxy groups such as methoxy, ethoxy, n-propoxy, isopropoxy, n-butoxy, isobutoxy, sec-butoxy, t-butoxy, n-pentyloxy, neopentyloxy, and n-hexyloxy.

The nitrous acid compound may include, for example, nitrous acid, methyl nitrite, ethyl nitrite, propyl nitrite, isopropyl nitrite, butyl nitrite, isobutyl nitrite, sec-butyl nitrite, t-butyl nitrite, pentyl nitrite, neopentyl nitrite, hexyl nitrite, nitrosyl chloride, and nitrosylsulfuric acid. The amount of nitrous acid compound to be used is usually in the range of 0.9 to 10 times greater moles, preferably 1 to 3 times greater moles, relative to the diketo compound (V).

The reaction is usually carried out in the presence of a base or an acid. When the reaction is carried out in the presence of a base, the base may include, for example, alkali metal hydroxides such as sodium hydroxide and potassium hydroxide; alkali metal alkoxides such as sodium methoxide, sodium ethoxide, and potassium t-butoxide; and hydrides of alkali metals or alkaline earth metals, such as sodium hydride and calcium hydride. These bases are used each solely or in admixture of two or more kinds of bases, and the amount of base to be used is usually in the range of 0.8 to 20 times greater moles, preferably 0.9 to 10 times greater moles, relative to the diketo compound (V).

When the reaction is carried out in the presence of an acid, the acid may include, for example, inorganic acids such as hydrogen chloride, hydrochloric acid, and sulfuric acid; and organic acids such as acetic acid, trifluoroacetic acid, and propionic acid. These acids are used each solely or in admixture of two or more kinds of acids, and the amount of acid to be used is usually in the range of 0.8 to 20 times greater moles, preferably 0.9 to 10 times greater moles, relative to the diketo compound (V).

The reaction can be carried out without solvent or can also be carried out in the presence of a solvent. The organic solvent is not particularly limited, so long as it is substantially inert to the reaction; and it may include, for example, alcohols such as water, methanol, ethanol, and isopropanol; aromatic hydrocarbons such as benzene, toluene, and xylene; aliphatic hydrocarbons such as hexane, cyclohexane, and heptane; halogenated hydrocarbons such as chlorobenzene, dichlorobenzene, chloroform, and 1,2-dichloroethane; and ethers such as diethyl ether and diisopropyl ether. These solvents are used each solely or in admixture of two or more kinds of solvents, and the amount of solvent to be used is usually at most 50 times greater by weight, relative to the diketo compound (V).

When the reaction is carried out without solvent, it is achieved, for example, by supplying nitrous acid compound (VI) to a mixture of diketo compound (V) and an acid or a base. Alternatively, a mixture of the nitrous acid compound and the acid may also be supplied to the diketo compound.

When the reaction is carried out in the presence of a solvent, it is achieved, for example, by supplying nitrous acid compound (VI) to a mixture of diketo compound (V) dissolved in an organic solvent and an acid or a base. Alternatively, a mixture of the nitrous acid compound and the acid may also be supplied to the diketo compound dissolved in an organic solvent. The reaction temperature is usually in the range of −50° C. to 80° C., preferably −30° C. to 50° C.

The α-oximino ester compound may be obtained in the organic layer, for example, by pouring the reaction mixture after the reaction into water, followed by the extraction with an organic solvent. The organic solvent may include, for example, aromatic hydrocarbons such as benzene, toluene, and xylene; aliphatic hydrocarbons such as hexane, cyclohexane, and heptane; halogenated hydrocarbons such as chlorobenzene, dichlorobenzene, chloroform, and 1,2-dichloroethane; ketones such as methyl isobutyl ketones; and ethers such as diethyl ether and diisopropyl ether.

The phase separation gives the α-oximino ester compound (VII) containing organic layer. The α-oximino ester compound (VII) can easily be isolated from the organic layer, for example, by a technique such as solvent evaporation, and it can be used in the next step without purification. Alternatively, the α-oximino ester compound (VII) containing organic layer may also be used as such a solution in the next step without concentration. As a matter of course, the α-oximino ester compound (VII) purified by an ordinary technique such as recrystallization or column chromatography can also be used in the next step.

Thus, the α-oximino ester compound of general formula (VII) is obtained. The α-oximino ester compound may include, for example, methyl 2-hydroximino-4-phenylbutanoate, methyl 4-(4-fluorophenyl)-2-hydroximinobutanoate, methyl 4-(3-chlorophenyl)-2-hydroximinobutanoate, methyl 4-(4-chlorophenyl)-2-hydroximinobutanoate, methyl 4-(2-bromophenyl)-2-hydroximinobutanoate, methyl 2-hydroximino-4-(2-nitrophenyl)butanoate, methyl 2-hydroximino-4-(4-nitrophenyl)butanoate, methyl 4-(4-chloro-2-nitrophenyl)-2-hydroximinobutanoate, methyl 4-(4-bromo-2-nitrophenyl)-2-hydroximinobutanoate, methyl 2-hydroximino-4-(3-trifluoromethylphenyl)butanoate, methyl 2-hydroximino-4-(2-methylphenyl)butanoate, methyl 4-(2,4-dimethylphenyl)-2-hydroximinobutanoate, methyl 2-hydroximino-4-(2-methoxyphenyl)butanoate, methyl 2-hydroximino-4-(4-methoxyphenyl)butanoate, methyl 4-(2,5-dimethoxyphenyl)-2-hydroximinobutanoate, methyl 4-(3,4-dimethoxyphenyl)-2-hydroximinobutanoate, methyl 2-hydroximino-4-(1-naphthyl)butanoate, methyl 2-hydroximino-4-(2-nitro-1-naphthyl)butanoate, methyl 2-hydroximino-4-(2-naphthyl)butanoate, methyl 4-(1-chloro-2-naphthyl)-2-hydroximinobutanoate, methyl 4-(1-bromo-2-naphthyl)-2-hydroximinobutanoate, methyl 2-hydroximino-4-(1-nitro-2-naphthyl)butanoate, methyl 2-hydroximinopentanoate, methyl 5-cyclohexyl-2-hydroximinopentanoate, methyl 2-hydroximino-5-phenylpentanoate, methyl 5-(3-chlorophenyl)-2-hydroximinopentanoate, methyl 2-hydroximino-5-(3-methoxyphenyl)pentanoate, methyl 2-hydroximino-5-(4-methoxyphenyl)pentanoate, methyl 5,5-diphenyl-2-hydroximinopentanoate, methyl 2-hydroximino-5-methoxy-5-phenylpentanoate, methyl 5-(4-chlorophenyl)-2-hydroximino-5-methoxypentanoate, methyl 2-hydroximino-5-isopropoxy-5-phenylpentanoate, methyl 2-hydroximino-5-isopropoxy-5-(4-methylphenyl)pentanoate, methyl 2-hydroximino-5-phenoxypentanoate, methyl 5-(4-fluorophenoxy)-2-hydroximinopentanoate, methyl 5-(2-bromo-4-methylphenoxy)-2-hydroximinopentanoate, methyl 5-(2,6-dibromo-4-methylphenoxy)-2-hydroximinopentanoate, methyl 2-hydroximinohexanoate, methyl 2-hydroximino-5-methylhexanoate, methyl 5,5-dimethyl-2-hydroximinohexanoate, methyl 2-hydroximino-5-phenylhexanoate, methyl 2-hydroximino-6-phenylhexanoate, methyl 2-hydroximino-6-phenoxyhexanoate, methyl 2-hydroximino-6-(2-methylphenoxy)hexanoate, methyl 2-hydroximino-6-(3-methylphenoxy)hexanoate, methyl 2-hydroximino-6-(4-methylphenoxy)hexanoate, methyl 2-hydroximino-6-(4-nitrophenoxy)hexanoate, methyl 6-(2,5-dimethylphenoxy)-2-hydroximinohexanoate, methyl 2-hydroximinoheptanoate, methyl 7-chloro-2-hydroximinoheptanoate, methyl 7-bromo-2-hydroximinoheptanoate, methyl 2-hydroximino-6-methylheptanoate, methyl 2-hydroximino-7-phenylheptanoate, methyl 2-hydroximino-7-phenoxyheptanoate, methyl 7-(4-t-butylphenoxy)-2-hydroximinoheptanoate, methyl 2-hydroximinooctanoate, methyl 2-hydroximino-7-methyloctanoate, methyl 2-hydroximino-8-phenyloctanoate, methyl 2-hydroximinononanoate, methyl 2-hydroximino-8-methylnonanoate, methyl 2-hydroximinodecanoate, methyl 2-hydroximino-10-phenoxydecanoate, ethyl 2-hydroximino-4-phenylbutanoate, ethyl 4-(4-fluorophenyl)-2-hydroximinobutanoate, ethyl 4-(3-chlorophenyl)-2-hydroximinobutanoate, ethyl 4-(4-chlorophenyl)-2-hydroximinobutanoate, ethyl 4-(2-bromophenyl)-2-hydroximinobutanoate, ethyl 2-hydroximino-4-(2-nitrophenyl)butanoate, ethyl 2-hydroximino-4-(4-nitrophenyl)butanoate, ethyl 4-(4-chloro-2-nitrophenyl)-2-hydroximinobutanoate, ethyl 4-(4-bromo-2-nitrophenyl)-2-hydroximinobutanoate, ethyl 2-hydroximino-4-(3-trifluoromethylphenyl)butanoate, ethyl 2-hydroximino-4-(2-methylphenyl)butanoate, ethyl 4-(2,4-dimethylphenyl)-2-hydroximinobutanoate, ethyl 2-hydroximino-4-(2-methoxyphenyl)butanoate, ethyl 2-hydroximino-4-(4-methoxyphenyl)butanoate, ethyl 4-(2,5-dimethoxyphenyl)-2-hydroximinobutanoate, ethyl 4-(3,4-dimethoxyphenyl)-2-hydroximinobutanoate, ethyl 2-hydroximino-4-(1-naphthyl)butanoate, ethyl 2-hydroximino-4-(2-nitro-1-naphthyl)butanoate, ethyl 2-hydroximino-4-(2-naphthyl)butanoate, ethyl 4-(1-chloro-2-naphthyl)-2-hydroximinobutanoate, ethyl 4-(1-bromo-2-naphthyl)-2-hydroximinobutanoate, ethyl 2-hydroximino-4-(1-nitro-2-naphthyl)butanoate, ethyl 2-hydroximinopentanoate, ethyl 5-cyclohexyl-2-hydroximinopentanoate, ethyl 2-hydroximino-5-phenylpentanoate, ethyl 5-(3-chlorophenyl)-2-hydroximinopentanoate, ethyl 2-hydroximino-5-(3-methoxyphenyl)pentanoate, ethyl 2-hydroximino-5-(4-methoxyphenyl)pentanoate, ethyl 5,5-diphenyl-2-hydroximinopentanoate, ethyl 2-hydroximino-5-methoxy-5-phenylpentanoate, ethyl 5-(4-chlorophenyl)-2-hydroximino-5-methoxypentanoate, ethyl 2-hydroximino-5-isopropoxy-5-phenylpentanoate, ethyl 2-hydroximino-5-isopropoxy-5-(4-methylphenyl)pentanoate, ethyl 2-hydroximino-5-phenoxypentanoate, ethyl 5-(4-fluorophenoxy)-2-hydroximinopentanoate, ethyl 5-(2-bromo-4-methylphenoxy)-2-hydroximinopentanoate, ethyl 5-(2,6-dibromo-4-methylphenoxy)-2-hydroximinopentanoate, ethyl 2-hydroximinohexanoate, ethyl 2-hydroximino-5-methylhexanoate, ethyl 5,5-dimethyl-2-hydroximinohexanoate, ethyl 2-hydroximino-5-phenylhexanoate, ethyl 2-hydroximino-6-phenylhexanoate, ethyl 2-hydroximino-6-phenoxyhexanoate, ethyl 2-hydroximino-6-(2-methylphenoxy)hexanoate, ethyl 2-hydroximino-6-(3-methylphenoxy)hexanoate, ethyl 2-hydroximino-6-(4-methylphenoxy)hexanoate, ethyl 2-hydroximino-6-(4-nitrophenoxy)hexanoate, ethyl 6-(2,5-dimethylphenoxy)-2-hydroximinohexanoate, ethyl 2-hydroximinoheptanoate, ethyl 7-chloro-2-hydroximinoheptanoate, ethyl 7-bromo-2-hydroximinoheptanoate, ethyl 2-hydroximino-6-methylheptanoate, ethyl 2-hydroximino-7-phenylheptanoate, ethyl 2-hydroximino-7-phenoxyheptanoate, ethyl 7-(4-t-butylphenoxy)-2-hydroximinoheptanoate, ethyl 2-hydroximinooctanoate, ethyl 2-hydroximino-7-methyloctanoate, ethyl 2-hydroximino-8-phenyloctanoate, ethyl 2-hydroximinononanoate, ethyl 2-hydroximino-8-methylnonanoate, ethyl 2-hydroximinodecanoate, ethyl 2-hydroximino-10-phenoxydecanoate, isopropyl 2-hydroximino-4-phenylbutanoate, isopropyl 4-(4-fluorophenyl)-2-hydroximinobutanoate, isopropyl 4-(3-chlorophenyl)-2-hydroximinobutanoate, isopropyl 4-(4-chlorophenyl)-2-hydroximinobutanoate, isopropyl 4-(2-bromophenyl)-2-hydroximinobutanoate, isopropyl 2-hydroximino-4-(2-nitrophenyl)butanoate, isopropyl 2-hydroximino-4-(4-nitrophenyl)butanoate, isopropyl 4-(4-chloro-2-nitrophenyl)-2-hydroximinobutanoate, isopropyl 4-(4-bromo-2-nitrophenyl)-2-hydroximinobutanoate, isopropyl 2-hydroximino-4-(3-trifluoromethylphenyl)butanoate, isopropyl 2-hydroximino-4-(2-methylphenyl)butanoate, isopropyl4-(2,4-dimethylphenyl)-2-hydroximinobutanoate, isopropyl 2-hydroximino-4-(2-methoxyphenyl)butanoate, isopropyl 2-hydroximino-4-(4-methoxyphenyl)butanoate, isopropyl 4-(2,5-dimethoxyphenyl)-2-hydroximinobutanoate, isopropyl 4-(3,4-dimethoxyphenyl)-2-hydroximinobutanoate, isopropyl 2-hydroximino-4-(1-naphthyl)butanoate, isopropyl 2-hydroximino-4-(2-nitro-1-naphthyl)butanoate, isopropyl 2-hydroximino-4-(2-naphthyl)butanoate, isopropyl 4-(1-chloro-2-naphthyl)-2-hydroximinobutanoate, isopropyl 4-(1-bromo-2-naphthyl)-2-hydroximinobutanoate, isopropyl 2-hydroximino-4-(1-nitro-2-naphthyl)butanoate, isopropyl 2-hydroximinopentanoate, isopropyl 5-cyclohexyl-2-hydroximinopentanoate, isopropyl 2-hydroximino-5-phenylpentanoate, isopropyl 5-(3-chlorophenyl)-2-hydroximinopentanoate, isopropyl 2-hydroximino-5-(3-methoxyphenyl)pentanoate, isopropyl 2-hydroximino-5-(4-methoxyphenyl)pentanoate, isopropyl 5,5-diphenyl-2-hydroximinopentanoate, isopropyl 2-hydroximino-5-methoxy-5-phenylpentanoate, isopropyl 5-(4-chlorophenyl)-2-hydroximino-5-methoxypentanoate, isopropyl 2-hydroximino-5-isopropoxy-5-phenylpentanoate, isopropyl 2-hydroximino-5-isopropoxy-5-(4-methylphenyl)pentanoate, isopropyl 2-hydroximino-5-phenoxypentanoate, isopropyl 5-(4-fluorophenoxy)-2-hydroximinopentanoate, isopropyl 5-(2-bromo-4-methylphenoxy)-2-hydroximinopentanoate, isopropyl 5-(2,6-dibromo-4-methylphenoxy)-2-hydroximinopentanoate, isopropyl 2-hydroximinohexanoate, isopropyl 2-hydroximino-5-methylhexanoate, isopropyl 5,5-dimethyl-2-hydroximinohexanoate, isopropyl 2-hydroximino-5-phenylhexanoate, isopropyl 2-hydroximino-6-phenylhexanoate, isopropyl 2-hydroximino-6-phenoxyhexanoate, isopropyl 2-hydroximino-6-(2-methylphenoxy)hexanoate, isopropyl 2-hydroximino-6-(3-methylphenoxy)hexanoate, isopropyl 2-hydroximino-6-(4-methylphenoxy)hexanoate, isopropyl 2-hydroximino-6-(4-nitrophenoxy)hexanoate, isopropyl 6-(2,5-dimethylphenoxy)-2-hydroximinohexanoate, isopropyl 2-hydroximinoheptanoate, isopropyl 7-chloro-2-hydroximinoheptanoate, isopropyl 7-bromo-2-hydroximinoheptanoate, isopropyl 2-hydroximino-6-methylheptanoate, isopropyl 2-hydroximino-7-phenylheptanoate, isopropyl 2-hydroximino-7-phenoxyheptanoate, isopropyl 7-(4-t-butylphenoxy)-2-hydroximinoheptanoate, isopropyl 2-hydroximinooctanoate, isopropyl 2-hydroximino-7-methyloctanoate, isopropyl 2-hydroximino-8-phenyloctanoate, isopropyl 2-hydroximinononanoate, isopropyl 2-hydroximino-8-methylnonanoate, isopropyl 2-hydroximinodecanoate, isopropyl 2-hydroximino-10-phenoxydecanoate, benzyl 2-hydroximino-4-phenylbutanoate, benzyl 4-(4-fluorophenyl)-2-hydroximinobutanoate, benzyl 4-(3-chlorophenyl)-2-hydroximinobutanoate, benzyl 4-(4-chlorophenyl)-2-hydroximinobutanoate, benzyl 4-(2-bromophenyl)-2-hydroximinobutanoate, benzyl 2-hydroximino-4-(2-nitrophenyl)butanoate, benzyl 2-hydroximino-4-(4-nitrophenyl)butanoate, benzyl 4-(4-chloro-2-nitrophenyl)-2-hydroximinobutanoate, benzyl 4-(4-bromo-2-nitrophenyl)-2-hydroximinobutanoate, benzyl 2-hydroximino-4-(3-trifluoromethylphenyl)butanoate, benzyl 2-hydroximino-4-(2-methylphenyl)butanoate, benzyl 4-(2,4-dimethylphenyl)-2-hydroximinobutanoate, benzyl 2-hydroximino-4-(2-methoxyphenyl)butanoate, benzyl 2-hydroximino-4-(4-methoxyphenyl)butanoate, benzyl 4-(2,5-dimethoxyphenyl)-2-hydroximinobutanoate, benzyl 4-(3,4-dimethoxyphenyl)-2-hydroximinobutanoate, benzyl 2-hydroximino-4-(1-naphthyl)butanoate, benzyl 2-hydroximino-4-(2-nitro-1-naphthyl)butanoate, benzyl 2-hydroximino-4-(2-naphthyl)butanoate, benzyl 4-(1-chloro-2-naphthyl)-2-hydroximinobutanoate, benzyl 4-(1-bromo-2-naphthyl)-2-hydroximinobutanoate, benzyl 2-hydroximino-4-(1-nitro-2-naphthyl)butanoate, benzyl 2-hydroximinopentanoate, benzyl 5-cyclohexyl-2-hydroximinopentanoate, benzyl 2-hydroximino-5-phenylpentanoate, benzyl 5-(3-chlorophenyl)-2-hydroximinopentanoate, benzyl 2-hydroximino-5-(3-methoxyphenyl)pentanoate, benzyl 2-hydroximino-5-(4-methoxyphenyl)pentanoate, benzyl 5,5-diphenyl-2-hydroximinopentanoate, benzyl 2-hydroximino-5-methoxy-5-phenylpentanoate, benzyl 5-(4-chlorophenyl)-2-hydroximino-5-methoxypentanoate, benzyl 2-hydroximino-5-isopropoxy-5-phenylpentanoate, benzyl 2-hydroximino-5-isopropoxy-5-(4-methylphenyl)pentanoate, benzyl 2-hydroximino-5-phenoxypentanoate, benzyl 5-(4-fluorophenoxy)-2-hydroximinopentanoate, benzyl 5-(2-bromo-4-methylphenoxy)-2-hydroximinopentanoate, benzyl 5-(2,6-dibromo-4-methylphenoxy)-2-hydroximinopentanoate, benzyl 2-hydroximinohexanoate, benzyl 2-hydroximino-5-methylhexanoate, benzyl 5,5-dimethyl-2-hydroximinohexanoate, benzyl 2-hydroximino-5-phenylhexanoate, benzyl 2-hydroximino-6-phenylhexanoate, benzyl 2-hydroximino-6-phenoxyhexanoate, benzyl 2-hydroximino-6-(2-methylphenoxy)hexanoate, benzyl 2-hydroximino-6-(3-methylphenoxy)hexanoate, benzyl 2-hydroximino- 6-(4-methylphenoxy)hexanoate, benzyl 2-hydroximino-6-(4-nitrophenoxy)hexanoate, benzyl 6-(2,5-dimethylphenoxy)-2-hydroximinohexanoate, benzyl 2-hydroximinoheptanoate, benzyl 7-chloro-2-hydroximinoheptanoate, benzyl 7-bromo-2-hydroximinoheptanoate, benzyl 2-hydroximino-6-methylheptanoate, benzyl 2-hydroximino-7-phenylheptanoate, benzyl 2-hydroximino-7-phenoxyheptanoate, benzyl 7-(4-t-butylphenoxy)-2- hydroximinoheptanoate, benzyl 2-hydroximinooctanoate, benzyl 2-hydroximino-7-methyloctanoate, benzyl 2-hydroximino-8-phenyloctanoate, benzyl 2-hydroximinononanoate, benzyl 2-hydroximino-8-methylnonanoate, benzyl 2-hydroximinodecanoate, benzyl 2-hydroximino-10-phenoxydecanoate, propyl 2-hydroximino-4-phenylbutanoate, butyl 2-hydroximino-4-phenylbutanoate, isobutyl 2-hydroximino-4-phenylbutanoate, sec-butyl 2-hydroximino-4-phenylbutanoate, t-butyl 2-hydroximino-4-phenylbutanoate, pentyl 2-hydroximino-4-phenylbutanoate, neopentyl 2-hydroximino-4-phenylbutanoate, hexyl 2-hydroximino-4-phenylbutanoate, p-nitrobenzyl 2-hydroximino-4-phenylbutanoate, 2-phenylethyl 2-hydroximino-4-phenylbutanoate, and t-butyl 2-hydroximino-4-(2-nitrophenyl)butanoate.

The α-oximino ester compound (VII) thus obtained is then reacted with an aldehyde compound in the presence of an acid to give the pyruvic acid compound (VIII).

As the acid, there is usually used an inorganic acid such as hydrochloric acid, sulfuric acid, or hydrobromic acid. The amount of acid to be used is usually at most 0.1 time greater moles, preferably in the range of 0.5 to 50 times greater moles, and more preferably in the range of 1 to 20 times greater moles, relative to the a-oximino ester compound (VII).

The aldehyde compound may include, for example, formaldehyde, formalin, paraformaldehyde, acetaldehyde, propionaldehyde, glyoxylic acid, and glyoxal.

The amount of aldehyde compound to be used is usually in the range of 0.8 to 15 times greater moles, preferably 0.9 to 10 times greater moles, relative to the a-oximino ester compound (VII).

The reaction is usually carried out in the presence of a solvent. The solvent is not particularly limited, so long as it is substantially inert to the reaction; and it may include, for example, water; aromatic hydrocarbons such as benzene, toluene, and xylene; aliphatic hydrocarbons such as hexane, cyclohexane, and heptane; halogenated hydrocarbons such as chlorobenzene, dichlorobenzene, chloroform, and 1,2-dichloroethane; ethers such as diethyl ether and diisopropyl ether; ketones such as methyl isobutyl ketone; alcohols such as methanol, ethanol, and isopropanol; amides such as N,N-dimethylformamide and N-methyl-2-pyrrolidone; sulfoxides such as dimethylsulfoxide; and nitrites such as acetonitrile. These organic solvents are used each solely or in admixture of two or more kinds of solvents, and the amount of solvent to be used is usually in the range of 0.2 to 50 times greater by weight, preferably 0.5 to 30 times greater by weight, relative to the α-oximino ester compound (VII).

The reaction is carried out, for example, by the addition of an aldehyde compound to a mixture of an a-oximino ester compound dissolved in an organic solvent with an acid. Alternatively, the acid may also be added to a mixture of the α-oximino ester compound dissolved in an organic solvent with the aldehyde compound; or the α-oximino ester compound dissolved in an organic solvent may also be added to a mixture of the aldehyde compound and the acid.

Furthermore, when the preceding step was carried out, for example, by the use of nitrosylsulfuric acid, the portion of the nitrosylsulfuric acid, which was consumed in the reaction, has become to sulfuric acid; therefore, the addition of an acid in this step is not particularly required, and for example, this step can be carried out, without separating the α-oximino ester compound (VII) from the reaction mixture in the preceding step, by the addition thereof as such a mixture with the acid to the aldehyde compound.

The reaction temperature is usually in the range of −10° C. to 100° C., preferably 0 ° C. to 80° C.

The pyruvic acid compound may be obtained in the organic layer, for example, by the phase separation of the reaction mixture. When the amount of water to be used in the reaction or the amount of organic solvent to be used in the reaction is small, it may sometimes be difficult to easily achieve the phase separation, in which case, however, the addition of a hydrophobic solvent or water may suitably be followed by the phase separation. The hydrophobic solvent may include, for example, aromatic hydrocarbons such as benzene, toluene, and xylene; aliphatic hydrocarbons such as hexane, cyclohexane, and heptane; halogenated hydrocarbons such as chlorobenzene, dichlorobenzene, chloroform, and 1,2-dichloroethane; ketones such as methyl isobutyl ketone; and ethers such as diethyl ether and diisopropyl ether.

The phase separation gives the pyruvic acid compound (VIII) containing organic layer, and a crude product of the pyruvic acid compound (VIII) can easily be separated from the organic layer, for example, by a technique such as solvent evaporation, and it can be used for the starting material in the present invention. Alternatively, the pyruvic acid compound (VIII) containing organic layer can also be used as such a solution, without concentration, for the starting material in the present invention.

Thus, the pyruvic acid compound of general formula (VIII) is obtained. The pyruvic acid compound may include, for example, methyl 2-oxo-4-phenylbutanoate, methyl 4-(4-fluorophenyl)-2-oxobutanoate, methyl 4-(3-chlorophenyl)-2-oxobutanoate, methyl 4-(4-chlorophenyl)-2-oxobutanoate, methyl 4-(2-bromophenyl)-2-oxobutanoate, methyl 4-(2-nitrophenyl)-2-oxobutanoate, methyl 4-(4-nitrophenyl)-2-oxobutanoate, methyl 4-(4-chloro-2-nitrophenyl)-2-oxobutanoate, methyl 4-(4-bromo-2-nitrophenyl)-2-oxobutanoate, methyl 2-oxo-4-(3-trifluoromethylphenyl)butanoate, methyl 4-(2-methylphenyl)-2-oxobutanoate, methyl 4-(2,4-dimethylphenyl)-2-oxobutanoate, methyl 4-(2-methoxyphenyl)-2-oxobutanoate, methyl 4-(4-methoxyphenyl)-2-oxobutanoate, methyl 4-(2,5-dimethoxyphenyl)-2-oxobutanoate, methyl 4-(3,4-dimethoxyphenyl)-2-oxobutanoate, methyl 4-(1-naphthyl)-2-oxobutanoate, methyl 4-(2-nitro-1-naphthyl)-2-oxobutanoate, methyl 4-(2-naphthyl)-2-oxobutanoate, methyl 4-(1-chloro-2-naphthyl)-2-oxobutanoate, methyl 4-(1-bromo-2-naphthyl)-2-oxobutanoate, methyl 4-(1-nitro-2-naphthyl)-2-oxobutanoate, methyl 2-oxopentanoate, methyl 5-cyclohexyl-2-oxopentanoate, methyl 2-oxo-5-phenylpentanoate, methyl 5-(3-chlorophenyl)-2-oxopentanoate, methyl 5-(3-methoxyphenyl)-2-oxopentanoate, methyl 5-(4-methoxyphenyl)-2-oxopentanoate, methyl 5,5-diphenyl-2-oxopentanoate, methyl 5-methoxy-2-oxo-5-phenylpentanoate, methyl 5-(4-chlorophenyl)-5-methoxy-2-oxopentanoate, methyl 5-isopropoxy-2-oxo-5-phenylpentanoate, methyl 5-isopropoxy-5-(4-methylphenyl)-2-oxopentanoate, methyl 2-oxo-5-phenoxypentanoate, methyl 5-(4-fluorophenoxy)-2-oxopentanoate, methyl 5-(2-bromo-4-methylphenoxy)-2-oxopentanoate, methyl 5-(2,6-dibromo-4-methylphenoxy)-2-oxopentanoate, methyl 2-oxohexanoate, methyl 5-methyl-2-oxohexanoate, methyl 5,5-dimethyl-2-oxohexanoate, methyl 2-oxo-5-phenylhexanoate, methyl 2-oxo-6-phenylhexanoate, methyl 2-oxo-6-phenoxyhexanoate, methyl 6-(2-methylphenoxy)-2-oxohexanoate, methyl 6-(3-methylphenoxy)-2-oxohexanoate, methyl 6-(4-methylphenoxy)-2-oxohexanoate, methyl 6-(4- nitrophenoxy)-2-oxohexanoate, methyl 6-(2,5-dimethylphenoxy)-2-oxohexanoate, methyl 2-oxoheptanoate, methyl 7-chloro-2-oxoheptanoate, methyl 7-bromo-2-oxoheptanoate, methyl 6-methyl-2-oxoheptanote, methyl 2-oxo-7-phenylheptanoate, methyl 2-oxo-7-phenoxyheptanoate, methyl 7-(4-t-butylphenoxy)-2-oxoheptanoate, methyl 2-oxooctanoate, methyl 7-methyl-2-oxooctanoate, methyl 2-oxo-8-phenyloctanoate, methyl 2-oxononanoate, methyl 8-methyl-2-oxononanoate, methyl 2-oxodecanoate, methyl 2-oxo-10-phenoxydecanoate, ethyl 2-oxo-4-phenylbutanoate, ethyl 4-(4-fluorophenyl)-2-oxobutanoate, ethyl 4-(3-chlorophenyl)-2-oxobutanoate, ethyl 4-(4-chlorophenyl)-2-oxobutanoate, ethyl 4-(2-bromophenyl)-2-oxobutanoate, ethyl 4-(2-nitrophenyl)-2-oxobutanoate, ethyl 4-(4-nitrophenyl)-2-oxobutanoate, ethyl 4-(4-chloro-2-nitrophenyl)-2-oxobutanoate, ethyl 4-(4-bromo-2-nitrophenyl)-2-oxobutanoate, ethyl 2-oxo-4-(3-trifluoromethylphenyl)butanoate, ethyl (2-methylphehenyl)-2-oxobutanoate, ethyl 4-(2,4-dimethylphenyl)-2-oxobutanoate, ethyl 4-(2-methoxyphenyl)-2-oxobutanoate, ethyl 4-(4-methoxyphenyl)-2-oxobutanoate, ethyl 4-(2,5-dimethoxyphenyl)-2-oxobutanoate, ethyl 4-(3,4-dimethoxyphenyl)-2-oxobutanoate, ethyl 4-(1-naphthyl)-2-oxobutanoate, ethyl 4-(2-nitro-1-naphthyl)-2-oxobutanoate, ethyl 4-(2-naphthyl)-2-oxobutanoate, ethyl 4-(1-chloro-2-naphthyl)-2-oxobutanoate, ethyl 4-(1-bromo-2-naphthyl)-2-oxobutanoate, ethyl 4-(1-nitro-2-naphthyl)-2-oxobutanoate, ethyl 2-oxopentanoate, ethyl 5-cyclohexyl-2-oxopentanoate, ethyl 2-oxo-5-phenylpentanoate, ethyl 5-(3-chlorophenyl)-2-oxopentanoate, ethyl 5-(3-methoxyphenyl)-2-oxopentanoate, ethyl 5-(4-methoxyphenyl)-2-oxopentanoate, ethyl 5,5-diphenyl-2-oxopentanoate, ethyl 5-methoxy-2-oxo-5-phenylpentanoate, ethyl 5-(4-chlorophenyl)-5-methoxy-2-oxopentanoate, ethyl 5-isopropoxy-2-oxo-5-phenylpentanoate, ethyl 5-isopropoxy-5-(4-methylphenyl)-2-oxopentanoate, ethyl 2-oxo-5-phenoxypentanoate, ethyl 5-(4-fluorophenoxy)-2-oxopentanoate, ethyl 5-(2-bromo-4-methylphenoxy)-2-oxopentanoate, ethyl 5-(2,6-dibromo-4-methylphenoxy)-2-oxopentanoate, ethyl 2-oxohexanoate, ethyl 5-methyl-2-oxohexanoate, ethyl 5,5-dimethyl-2-oxohexanoate, ethyl 2-oxo-5-phenylhexanoate, ethyl 2-oxo-6-phenylhexanoate, ethyl 2-oxo-6-phenoxyhexanoate, ethyl 6-(2-methylphenoxy)-2-oxohexanoate, ethyl 6-(3-methylphenoxy)-2-oxohexanoate, ethyl 6-(4-methylphenoxy)-2-oxohexanoate, ethyl 6-(4-nitrophenoxy)-2-oxohexanoate, ethyl 6-(2,5-dimethylphenoxy)-2-oxohexanoate, ethyl 2-oxoheptanoate, ethyl 7-chloro-2-oxoheptanoate, ethyl 7-bromo-2-oxoheptanoate, ethyl 6-methyl-2-oxoheptanoate, ethyl 2-oxo-7-phenylheptanoate, ethyl 2-oxo-7-phenoxyheptanoate, ethyl 7-(4-t-butylphenoxy)-2-oxoheptanoate, ethyl 2-oxooctanoate, ethyl 7-methyl-2-oxooctanoate, ethyl 2-oxo-8-phenyloctanoate, ethyl 2-oxononanoate, ethyl 8-methyl-2-oxononanoate, ethyl 2-oxodecanoate, ethyl 2-oxo-10-phenoxydecanoate, isopropyl 2-oxo-4-phenylbutanoate, isopropyl 4-(4-fluorophenyl)-2-oxobutanoate, isopropyl 4-(3-chlorophenyl)-2-oxobutanoate, isopropyl 4-(4-chlorophenyl)-2-oxobutanoate, isopropyl 4-(2-bromophenyl)-2-oxobutanoate, isopropyl 4-(2-nitrophenyl)-2-oxobutanoate, isopropyl 4-(4-nitrophenyl)-2-oxobutanoate, isopropyl 4-(4-chloro-2-nitrophenyl)-2-oxobutanoate, isopropyl 4-(4-bromo-2-nitrophenyl)-2-oxobutanoate, isopropyl 2-oxo-4-(3-trifluoromethylphenyl)butanoate, isopropyl 4-(2-methylphenyl)-2-oxobutanoate, isopropyl 4-(2,4-dimethylphenyl)-2-oxobutanoate, isopropyl 4-(2-methoxyphenyl)-2-oxobutanoate, isopropyl 4-(4-methoxyphenyl)-2-oxobutanoate, isopropyl 4-(2,5-dimethoxyphenyl)-2-oxobutanoate, isopropyl 4-(3,4-dimethoxyphenyl)-2-oxobutanoate, isopropyl 4-(1-naphthyl)-2-oxobutanoate, isopropyl 4-(2-nitro-1-naphthyl)-2-oxobutanoate, isopropyl 4-(2-naphthyl)-2-oxobutanoate, isopropyl 4-(1-chloro-2-naphthyl)-2-oxobutanoate, isopropyl 4-(1-bromo-2-naphthyl)-2-oxobutanoate, isopropyl 4-(1-nitro-2-naphthyl)-2-oxobutanoate, isopropyl 2-oxopentanoate, isopropyl 5-cyclohexyl-2-oxopentanoate, isopropyl 2-oxo-5-phenylpentanoate, isopropyl 5-(3-chlorophenyl)-2-oxopentanoate, isopropyl 5-(3-methoxyphenyl)-2-oxopentanoate, isopropyl 5-(4-methoxyphenyl)-2-oxopentanoate, isopropyl 5,5-diphenyl-2-oxopentanoate, isopropyl 5-methoxy-2-oxo-5-phenylpentanoate, isopropyl 5-(4-chlorophenyl)-5-methoxy-2-oxopentanoate, isopropyl 5-isopropoxy-2-oxo-5-phenylpentanoate, isopropyl 5-isopropoxy-5-(4-methylphenyl)-2-oxopentanoate, isopropyl 2-oxo-5-phenoxypentanoate, isopropyl 5-(4-fluorophenoxy)-2-oxopentanoate, isopropyl 5-(2-bromo-4-methylphenoxy)-2-oxopentanoate, isopropyl 5-(2,6-dibromo-4-methylphenoxy)-2-oxopentanoate, isopropyl 2-oxohexanoate, isopropyl 5-methyl-2-oxohexanoate, isopropyl 5,5-dimethyl-2-oxohexanoate, isopropyl 2-oxo-5-phenylhexanoate, isopropyl 2-oxo-6-phenylhexanoate, isopropyl 2-oxo-6-phenoxyhexanoate, isopropyl 6-(2-methylphenoxy)-2-oxohexanoate, isopropyl 6-(3-methylphenoxy)-2-oxohexanoate, isopropyl 6-(4-methylphenoxy)-2-oxohexanoate, isopropyl 6-(4-nitrophenoxy)-2-oxohexanoate, isopropyl 6-(2,5-dimethylphenoxy)-2-oxohexanoate, isopropyl 2-oxoheptanoate, isopropyl 7-chloro-2-oxoheptanoate, isopropyl 7-bromo-2-oxoheptanoate, isopropyl 6-methyl-2-oxoheptanoate, isopropyl 2-oxo-7-phenylheptanoate, isopropyl 2-oxo-7-phenoxyheptanoate, isopropyl 7-(4-t-butylphenoxy)-2-oxoheptanoate, isopropyl 2-oxooctanoate, isopropyl 7-methyl-2-oxooctanoate, isopropyl 2-oxo-8-phenyloctanoate, isopropyl 2-oxononanoate, isopropyl 8-methyl-2-oxononanoate, isopropyl 2-oxodecanoate, isopropyl 2-oxo-10-phenoxydecanoate, benzyl 2-oxo-4-phenylbutanoate, benzyl 4-(4-fluorophenyl)-2-oxobutanoate, benzyl 4-(3-chlorophenyl)-2-oxobutanoate, benzyl 4-(4-chlorophenyl)-2-oxobutanoate, benzyl 4-(2-bromophenyl)-2-oxobutanoate, benzyl 4-(2-nitrophenyl)-2-oxobutanoate, benzyl 4-(4-nitrophenyl)-2-oxobutanoate, benzyl 4-(4-chloro-2-nitrophenyl)-2-oxobutanoate, benzyl 4-(4-bromo-2-nitrophenyl)-2-oxobutanoate, benzyl 4-(2-methylphenyl)-2-oxobutanoate, benzyl 2-oxo-4-(3-trifluoromethylphenyl)butanoate, benzyl 4-(2,4-dimethylphenyl)-2-oxobutanoate, benzyl 4-(2-methoxyphenyl)-2-oxobutanoate, benzyl 4-(4-methoxyphenyl)-2-oxobutanoate, benzyl 4-(2,5-dimethoxyphenyl)-2-oxobutanoate, benzyl 4-(3,4-dimethoxyphenyl)-2-oxobutanoate, benzyl 4-(1-naphthyl)-2-oxobutanoate, benzyl 4-(2-nitro-1-naphthyl)-2-oxobutanoate, benzyl 4-(2-naphthyl)-2-oxobutanoate, benzyl 4-(1-chloro-2-naphthyl)-2-oxobutanoate, benzyl 4-(1-bromo-2-naphthyl)-2-oxobutanoate, benzyl 4-(1-nitro-2-naphthyl)-2-oxobutanoate, benzyl 2-oxopentanoate, benzyl 5-cyclohexyl-2-oxopentanoate, benzyl 2-oxo-5-phenylpentanoate, benzyl 5-(3-chlorophenyl)-2-oxopentanoate, benzyl 5-(3-methoxyphenyl)-2-oxopentanoate, benzyl 5-(4-methoxyphenyl)-2-oxopentanoate, benzyl 5,5-diphenyl-2-oxopentanoate, benzyl 5-methoxy-2-oxo-5-phenylpentanoate, benzyl 5-(4-chlorophenyl)-5-methoxy-2-oxopentanoate, benzyl 5-isopropoxy-2-oxo-5-phenylpentanoate, benzyl 5-isopropoxy-5-(4-methylphenyl)-2-oxopentanoate, benzyl 2-oxo-5-phenoxypentanoate, benzyl 5-(4-fluorophenoxy)-2-oxopentanoate, benzyl 5-(2-bromo-4-methylphenoxy)-2-oxopentanoate, benzyl 5-(2,6-dibromo-4-methylphenoxy)-2-oxopentanoate, benzyl 2-oxohexanoate, benzyl 5-methyl-2-oxohexanoate, benzyl 5,5-dimethyl-2-oxohexanoate, benzyl 2-oxo-5-phenylhexanoate, benzyl 2-oxo-6-phenylhexanoate, benzyl 2-oxo-6-phenoxyhexanoate, benzyl 6-(2-methylphenoxy)-2-oxohexanoate, benzyl 6-(3-methylphenoxy)-2-oxohexanoate, benzyl 6-(4-methylphenoxy)-2-oxohexanoate, benzyl 6-(4-nitrophenoxy)-2-oxohexanoate, benzyl 6-(2,5-dimethylphenoxy)-2-oxohexanoate, benzyl 2-oxoheptanoate, benzyl 7-chloro-2-oxoheptanoate, benzyl 7-bromo-2-oxoheptanoate, benzyl 6-methyl-2-oxoheptanoate, benzyl 2-oxo-7-phenylheptanoate, benzyl 2-oxo-7-phenoxyheptanoate, benzyl 7-(4-t-butylphenoxy)-2-oxoheptanoate, benzyl 2-oxooctanoate, benzyl 7-methyl-2-oxooctanoate, benzyl 2-oxo-8-phenyloctanoate, benzyl 2-oxononanoate, benzyl 8-methyl-2-oxononanoate, benzyl 2-oxodecanoate, benzyl 2-oxo-10-phenoxydecanoate, propyl 2-oxo-4-phenylbutanoate, butyl 2-oxo-4-phenylbutanoate, isobutyl 2-oxo-4-phenylbutanoate, sec-butyl 2-oxo-4-phenylbutanoate, t-butyl 2-oxo-4-phenylbutanoate, pentyl 2-oxo-4-phenylbutanoate, neopentyl 2-oxo-4-phenylbutanoate, hexyl 2-oxo-4-phenylbutanoate, p-nitrobenzyl 2-oxo-4-phenylbutanoate, 2-phenylethyl 2-oxo-4-phenylbutanoate, and t-butyl 4-(2-nitrophenyl)-2-oxobutanoate.

The adduct of a pyruvic acid compound with a bisulfite, which adduct is obtained by subjecting the crude product of pyruvic acid compound (VIII) thus obtained to the purification method of the present invention, may include bisulfite adducts of the above pyruvic acid compounds (VIII). The pyruvic acid compounds can be simply and easily purified by the purification of the bisulfite adducts obtained. The production process makes it possible to achieve the production of pyruvic acid compounds (VIII) with higher purity without purifying any intermediate in the production of the pyruvic acid compounds (VIII) that serve as the starting material, and hence, it was advantageous from an industrial point of view.

Furthermore, the bisulfite adducts of pyruvic acid compounds (VIII) produced by the present invention are novel compounds, and the use of these bisulfite adducts makes it possible to produce pyruvic acid compounds (VIII) with higher purity, which compounds are useful as intermediates for drugs, α-amino acids, or other products.

EXAMPLES

The present invention will be further illustrated by the following Examples; however, the present invention is not limited to these Examples.

In the following Examples, the reagent of sodium hydrogensulfite was commercially available. This was a mixture of sodium hydrogensulfite and sodium pyrosulfite, and the net sulfite content in the mixture was 58.5% by weight.

Example 1

A mixture of 1666 g (9.00 mol) of (2-bromoethyl)benzene, 1555 g (11.3 mol) of potassium carbonate, and 1419 g of n-heptane (which mixture had a water content of 0.7% by weight, relative to the potassium carbonate) was heated to 95° C., and 1053 g (8.10 mol) of ethyl 3-oxobutanoate was added dropwise at the same temperature over 4 hours. The mixture was stirred at the same temperature for 4 hours, to which 622 g (4.50 mol) of potassium carbonate and 933 g of n-heptane were added, and the mixture was further stirred at 95° C. for 10 hours. The reaction mixture was cooled to 70° C., and after the addition of 3543 g of water, was subjected to phase separation. The organic layer was washed with 1824 g of 3% aqueous sodium sulfate solution and then concentrated under reduced pressure to give 1745 g of the crude product of ethyl 3-oxo-2-(2-phenylethyl)butanoate. In the crude product, 62.3% by weight of ethyl 3-oxo-2-(2-phenylethyl)butanoate (52% yield) and 28.5% by weight of (2-bromoethyl)benzene were contained. This crude product was used as such in the next step without purification.

Then, 1050 g (2.79 mol) of the crude product of ethyl 3-oxo-2-(2-phenylethyl)butanoate thus obtained was cooled to 5° C., to which 908 g (3.14 mol) of 44% nitrosylsulfuric acid/sulfuric acid solution was added dropwise at 2–5° C. over 3.6 hours, and the mixture was stirred at the same temperature for 3.8 hours. In another flask, 654 g of water and 1961 g of toluene were placed and then cooled to 5° C., to which the above reaction solution was added dropwise at the same temperature over 50 minutes, and the mixture was warmed to 20° C. and then stirred for 1 hour. The reaction mixture was subjected to phase separation, and the oil layer was washed with 654 g of water to give 2951 g of a toluene solution containing ethyl 2-hydroximino-4-phenylbutanoate. In the toluene solution, 17.2% by weight of ethyl 2-hydroximino-4-phenylbutanoate (82% yield) and 10.3% by weight of (2-bromoethyl)benzene were contained. This toluene solution was used as such in the next step without purification.

To 1476 g (1.15 mol) of the toluene solution of ethyl 2-hydroximino-4-phenylbutanoate thus obtained were added 579 g (5.72 mol) of 36% hydrochloric acid and then added dropwise 232 g (2.86 mol) of 37% aqueous formaldehyde solution at 20° C. over 1 hour, and the mixture was stirred at the same temperature for 22 hours. The reaction mixture was subjected to phase separation, and the oil layer was washed with 373 g of 5% aqueous sodium carbonate solution and then with 318 g of water to give 1421 g of a toluene solution containing ethyl 2-oxo-4-phenylbutanoate. In the toluene solution, 15.6% by weight of ethyl 2-oxo-4-phenylbutanoate (94% yield) and 10.9% by weight of (2-bromoethyl)benzene were contained. The analysis by gas chromatography revealed that the percent area free of the solvent was 55.1% for ethyl 2-oxo-4-phenylbutanoate, 35.5% for (2-bromoethyl)benzene, and 9.4% in total for the other impurities.

Then, 62.2 g (47 mmol) of the toluene solution of ethyl 2-oxo-4-phenylbutanoate was added dropwise to a mixture of 6.4 g (59 mmol) of sodium hydrogensulfite, 25.4 g of water, and 12.8 g of toluene at 50° C. over 1.5 hours, and the mixture was stirred at the same temperature for 3 hours. The reaction mixture had pH 4.3. The reaction mixture was subjected to phase separation to give 42.9 g of the water layer containing 11.7 g (80% yield) of a sodium hydrogensulfite adduct of ethyl 2-oxo-4-phenylbutanoate. The separated oil layer, after the further addition of 2.9 g (27 mmol) of sodium hydrogen sulfite and 12.2 g of water, was stirred at 22° C. for 4 hours. The reaction mixture had pH 3.5. The reaction mixture was subjected to phase separation to give 16.5 g of the water layer containing 2.7 g (18% yield) of the sodium hydrogensulfite adduct of ethyl 2-oxo-4-phenylbutanoate. The water layers were combined and then washed once with 40.4 g of toluene, to which 40.0 g of toluene was added and 5.2 g (52 mmol) of 98% sulfuric acid was then added dropwise at 50° C. over 10 minutes, and the mixture was further stirred at the same temperature for 1 hour. The reaction mixture was subjected to phase separation, and the toluene layer was washed with 10 g of water and then concentrated to give 9.0 g of an oil containing 8.8 g (92% yield) of ethyl 2-oxo-4-phenylbutanoate. The analysis by gas chromatography revealed that the percent area free of the solvent was 96.9% for ethyl 2-oxo-4-phenylbutanoate and less than 0.06% for (2-bromoethyl)benzene, and was reduced to 3.1% in total for the other impurities.

Example 2

First, 62.0 g (47 mmol) of a toluene solution of the ethyl 2-oxo-4-phenylbutanoate prepared in Example 1 was added dropwise to a mixture of 6.4 g (59 mmol) of sodium hydrogensulfite, 25.7 g of water and 12.4 g of toluene at 22° C. over 1.5 hours, and the mixture was stirred at the same temperature for 3 hours. The reaction mixture had pH 4.3. The reaction mixture was subjected to phase separation to give 42.9 g of the water layer containing 13.8 g (94% yield) of a sodium hydrogensulfite adduct of ethyl 2-oxo-4-phenylbutanoate. The separated oil layer, after the further addition of 2.9 g (26 mmol) of sodium hydrogensulfite and 11.8 g of water, was stirred at 22° C. for 4 hours. The reaction mixture had pH 3.6. The reaction mixture was subjected to phase separation to give 14.6 g of the water layer containing 0.5 g (3% yield) of the sodium hydrogensulfite adduct of ethyl 2-oxo-4-phenylbutanioate. The water layers were combined, to which 40.2 g of toluene was added and 5.2 g (52 mmol) of 98% sulfuric acid was then added dropwise at 22° C. over 10 minutes, and the mixture was warmed to 50° C. and then stirred at 50° C. for 1 hour. The reaction mixture was subjected to phase separation, and the toluene layer was washed with 10 g of water and then concentrated to give 9.6 g of an oil containing 9.1 g (96% yield) of ethyl 2-oxo-4-phenylbutanoate. The analysis by gas chromatography revealed that the percent area free of the solvent was 95.4% for ethyl 2-oxo-4-phenylbutanoate and 1.1% for (2-bromoethyl)benzene, and was reduced to 3.5% in total for the other impurities.

Example 3

To an aqueous solution of 3.9 g (36 mmol) of sodium hydrogensulfite, 15.8 g of water, and 0.34 g (1.5 mmol) of benzyltriethylammomium chloride, was added dropwise 39.6 g of a toluene solution containing 6.2 g (30 mmol) of the ethyl 2-oxo-4-phenylbutanoate prepared in Example 1 at 50° C. over 24 hours, and the mixture was stirred at the same temperature for 4 hours. To this was added 1.5 ml of 5% aqueous sodium hydroxide solution so that the pH of the reaction mixture was controlled to 5.0, and the mixture was stirred at room temperature for 13 hours. The reaction mixture was subjected to phase separation to give the water layer containing 9.1 g (98% yield) of a sodium hydrogensulfite adduct of ethyl 2-oxo-4-phenylbutanoate. The water layer was heated to 50° C. and then washed with 15 ml of toluene, to which 23.8 g of toluene was then added and 3.5 g (35 mmol) of 98% sulfuric acid was then added dropwise at the same temperature over 5 minutes, and the mixture was further stirred at the same temperature for 1 hour. The reaction mixture was subjected to phase separation, and the toluene layer was washed with 6.9 g of water and then concentrated to give 5.7 g of an oil containing 5.4 g (89% yield) of ethyl 2-oxo-4-phenylbutanoate. The analysis by gas chromatography revealed that the percent area free of the solvent was 95.9% for ethyl 2-oxo-4-phenylbutanoate and 0.13% for (2-bromoethyl)benzene, and was reduced to 4.0% in total for the other impurities.

Example 4

A mixture of 2.19 g of ethyl 2-oxo-4-phenylbutanoate (94% purity, 10 mmol), 6.06 g of toluene, 1.10 g (10 mmol) of sodium hydrogensulfite, and 4.39 g of water was stirred at 50° C. for 7 hours, cooled to 25° C., and then further stirred at the same temperature for 8 hours. The reaction mixture was subjected to phase separation, and the water layer was washed with 5 ml of toluene and then freeze-dried to give 2.63 g of a sodium hydrogensulfite adduct of ethyl 2-oxo-4-phenylbutanoate.

$^1$H-NMR of the sodium hydrogensulfite adduct of ethyl 2-oxo-4-phenylbutanoate (270 MHz, DMSO-$d_6$): δ1.20 (t, 3H, J=7.1 Hz), 1.95–2.15 (m, 1H), 2.2–2.5 (m, 2H), 2.60–2.80 (m, 1H), 3.95–4.25 (m, 2H), 5.44 (s, 1H), 7.05–7.2 (m, 3H), 7.2–7.35 (m, 2H)

Example 5

First, 62.0 g (47 mmol) of the toluene solution of ethyl 2-oxo-4-phenylbutanoate prepared in Example 1 was added dropwise to a mixture of 6.4 g (59 mmol) of sodium hydrogensulfite, 25.0 g of water, and 12.5 g of toluene at 22° C. over 70 minutes, and the mixture was stirred at the same temperature for 1 hour. The reaction mixture had pH 4.3. The reaction mixture was subjected to phase separation to give 42.3 g of the water layer containing 14.1 g (97% yield) of a sodium hydrogensulfite adduct of ethyl 2-oxo-4-phenylbutanoate.

Example 6

The reaction was carried out in the same manner as described in Example 5, except that the reaction was carried out at 10° C. Thus, 42.6 g of the water layer containing 14.4 g (99% yield) of a sodium hydrogensulfite adduct of ethyl 2-oxo-4-phenylbutanoate was obtained.

Example 7

The reaction was carried out in the same manner as described in Example 5, except that the reaction was carried out at 35° C. Thus, 41.3 g of the water layer containing 13.6 g (93% yield) of a sodium hydrogensulfite adduct of ethyl 2-oxo-4-phenylbutanoate was obtained.

Example 8

The reaction was carried out in the same manner as described in Example 5, except that the reaction was carried out at 45° C. Thus, 40.8 g of the water layer containing 12.6 g (86% yield) of a sodium hydrogensulfite adduct of ethyl 2-oxo-4-phenylbutanoate was obtained.

Example 9

To a mixture (pH 4.2) of 62.0 g (47 mmol) of the toluene solution of ethyl 2-oxo-4-phenylbutanoate prepared in Example 1, 9.6 g (88 mmol) of sodium hydrogensulfite, 50 g of water, and 12.5 g of toluene was added 1.5 g of 10% sodium hydroxide at 50° C. so that the pH of the reaction mixture was controlled to 5.0, and the mixture was further stirred at the same temperature for 0.5 hour. The reaction mixture was subjected to phase separation to give 70.1 g of the water layer containing 12.3 g (85% yield) of a sodium hydrogensulfite adduct of ethyl 2-oxo-4-phenylbutanoate.

Example 10

The reaction was carried out in the same manner as described in Example 9, except that the pH of the reaction mixture was controlled to 5.9 by the addition of 7.7 g of 10% sodium hydroxide. Thus, 74.5 g of the water layer containing 11.3 g (77% yield) of a sodium hydrogensulfite adduct of ethyl 2-oxo-4-phenylbutanoate.

Example 11

To a mixture of 8.46 g (46 mmol) of (2-bromoethyl) benzene, 6.55 g (50 mmol) of ethyl 3-oxo-butanoate, and 4.23 g of toluene were added 15.8 g (115 mmol) of potassium carbonate and 0.21 g of water, and the mixture was heated to 75° C. and then stirred at the same temperature for 14.3 hours. The reaction mixture was cooled to 70° C., and after the addition of 21.4 g of water and 1.7 g of toluene, was subjected to phase separation. The organic layer was washed twice with 10.7 g of water and then concentrated under reduced pressure to give 10.4 g of the crude product of ethyl 3-oxo-2-(2-phenylethyl)butanoate. In the crude product, 79.5% by weight (77% yield) of ethyl 3-oxo-2-(2-phenylethyl)butanoate and 7.7% by weight of (2-bromoethyl)benzene were contained. This crude product was used as such in the next step without purification.

To 10.4 g (35 mmol) of the crude product of ethyl 3-oxo-2-(2-phenylethyl)butanoate thus obtained was added 12.4 g of toluene, and the mixture was cooled to 2° C., to which 11.9 g (41 mmol) of 44% nitrosylsulfuric acid/ sulfuric acid solution was added dropwise at 0–2° C. over 6 hours, and the mixture was further stirred at the same temperature for 2 hours. In another flask, 8.2 g of water and 12.4 g of toluene were placed and then cooled to 5° C., to which a mixture of the above reaction solution and 0.8 g of 98% sulfuric acid was added dropwise at the same temperature over 1 hour, and the mixture was warmed to 20° C. and then stirred for 1 hour. The reaction mixture was subjected to phase separation, and the oil layer was washed twice with 8.2 g of 5% aqueous sodium chloride solution to give 34.3 g of a toluene solution containing ethyl 2-hydroximino-4-phenylbutanoate. In the toluene solution, 19.5% by weight (86% yield) of ethyl 2-hydroximino-4-phenylbutanoate and 2.3% by weight of (2-bromoethyl)benzene were contained. This toluene solution was used as such in the next step without purification.

To 34.3 g (30 mmol) of the toluene solution of ethyl 2-hydroximino-4-phenylbutanoate thus obtained were added 18.4 g (182 mmol) of 36% hydrochloric acid and then added dropwise 8.5 g (91 mol) of 37% aqueous formaldehyde solution at 23° C. over 1 hour, and the mixture was stirred at the same temperature for 12 hours. The reaction mixture was subjected to phase separation, and the oil layer was washed with 6.9 g of 5% aqueous sodium chloride solution and then with 6.9 g of water to give, after the addition of 3 ml of toluene, 35.0 g of a toluene solution containing ethyl 2-oxo-4-phenylbutanoate. In the toluene solution, 17.7% by weight (97% yield) of ethyl 2-oxo-4-phenylbutanoate and 2.3% by weight of (2-bromoethyl) benzene were contained. The analysis by gas chromatography revealed that the percent area free of the solvent was 76.0% for ethyl 2-oxo-4-phenylbutanoate and 9.7% for (2-bromoethyl)benzene. This toluene solution was used as such in the next step without purification.

Then, 35.0 g (30 mmol) of the toluene solution of ethyl 2-oxo-4-phenylbutanoate thus obtained was added dropwise to a mixture of 3.9 g (36 mmol) of sodium hydrogensulfite, 15.8 g of water, and 6.2 g of toluene at 20° C. over 1.5 hours, and the mixture was stirred at the same temperature for 2 hours. The reaction mixture was subjected to phase separation to give 26.4 g of the water layer containing 8.9 g (96% yield) of a sodium hydrogensulfite adduct of ethyl 2-oxo-4-phenylbutanoate. The separated oil layer, after the further addition of 2.0 g (18 mmol) of sodium hydrogensulfite and 7.9 g of water, was stirred at 20° C. for 2 hours and then subjected to phase separation to give 10.1 g of the water layer containing 0.25 g (3% yield) of the sodium hydrogensulfite adduct of ethyl 2-oxo-4-phenylbutanoate. The water layers were combined and then washed once with 6.2 g of toluene, to which 17.3 g of toluene was added and 3.5 g (35 mmol) of 98% sulfuric acid was then added dropwise at 50° C. over 0.5 hour, and the mixture was further stirred at the same temperature for 2 hour. The reaction mixture was subjected to phase separation, and the toluene layer was washed with 6.9 g of water and then concentrated to give 6.0 g of an oil containing 5.6 g (92% yield) of ethyl 2-oxo-4-phenylbutanoate. The analysis by gas chromatography revealed that the percent area free of the solvent was 94.2% for ethyl 2-oxo-4-phenylbutanoate and less than 0.06% for (2-bromoethyl)benzene.

Reference Example 1

To a mixture of 55.5 g (300 mmol) of (2-bromoethyl) benzene and 42.9 g (330 mmol) of ethyl 3-oxobutanoate were added 124 g (894 mmol) of potassium carbonate and 2.49 g of water, and the mixture was heated to 70° C. and then stirred at the same temperature for 15 hours. The reaction mixture, after the addition of 198 g of water and 27.8 g of toluene, was subjected to phase separation. The organic layer was washed twice with 70.1 g of water and then concentrated under reduced pressure to give 70.4 g of the crude product of ethyl 3-oxo-2-(2-phenylethyl) butanoate. The ethyl 3-oxo-2-(2-phenylethyl)butanoate content in the crude product was 84.4% by weight (86% yield).

Reference Example 2

To 16.9 g of the crude product containing 9.4 g (40 mmol) of ethyl 3-oxo-2-(2-phenylethyl)butanoate obtained in accordance with Reference Example 1 was added 14.1 g of toluene, and the mixture was cooled to −20° C., to which 13.1 g (45 mmol) of 44% nitrosylsulfuric acid/sulfuric acid solution was added dropwise at the same temperature over 4.5 hours. The mixture was further stirred at the same temperature for 4 hours and then warmed to room temperature. In another flask, 9.3 g of water and 13.9 g of toluene were placed and then cooled to 5° C., to which the above reaction solution was added dropwise at the same temperature over 0.5 hour, and the mixture was warmed to 20° C. and then stirred 1 hour. The reaction mixture was subjected to phase separation, and the oil layer was washed twice with 9.3 g of water to give 44.9 g of a toluene solution containing ethyl 2-hydroximino-4-phenylbutanoate. The ethyl 2-hydroximino-4-phenylbutanoate content in the toluene solution was 17.4% by weight (90% yield).

Reference Example 3

In the same manner as described in Reference Example 1, except that 55.5 g (300 mmol) of (2-bromoethyl)benzene, 42.9 g (330 mmol) of ethyl 3-oxobutanoate, 27.8 g of toluene, 103 g (748 mmol) of potassium carbonate, and 2.08 g of water were used, 77.4 g of the crude product of ethyl 3-oxo-2-(2-phenylethyl)butanoate was obtained. The ethyl 3-oxo-2-(2-phenylethyl)butanoate content in the crude content was 68.9% by weight (77% yield).

Comparative Example

The alkylation was carried out in the same manner as described in Reference Example 3, except that water was not added. Thus, 90.6 g of the crude product of ethyl 3-oxo-2-(2-phenylethyl)butanoate was obtained. The ethyl 3-oxo-2-(2-phenylethyl)butanoate content in the crude product was 38.1% by weight (50% yield).

Example 12

In accordance with Example 1, a toluene solution containing 15.3% by weight of ethyl 2-oxo-4-phenylbutanoate and 10.7% by weight of (2-bromoethyl)benzene was prepared. The analysis by gas chromatography revealed that the percent area free of the solvent was 54.6% for ethyl 2-oxo-4-phenylbutanoate and 36.6% for (2-bromoethyl)benzene, and the other impurities were contained at 8.8% in total. Then, 40.9 g (30 mmol) of the toluene solution was added dropwise to a mixture of 7.1 g (36 mmol) of 50% aqueous ammonium hydrogensulfite solution and 14.3 g of water at 10° C. over 0.5 hour, and the mixture was stirred at the same temperature for 4 hours. The reaction mixture was subjected to phase separation and then washed with 6.0 g of toluene to give 28.4 g of the water layer containing 90 g (95% yield) of an ammonium hydrogensulfite adduct of ethyl 2-oxo-4-phenylbutanoate. The toluene layers obtained by the phase separation and the washing were combined and then analyzed by gas chromatography, revealing that 11.2% by weight (99.7% recovery) of (2-bromoethyl)benzene was contained in 39.1 g of the combined toluene layer. On the other hand, to 28.4 g of the water layer obtained by the phase separation and the washing, was added 18.2 g of toluene and then added dropwise 3.7 g (37 mmol) of 98% sulfuric acid at 50° C. over 15 minutes, and the mixture was further stirred at the same temperature for 2 hours. The reaction mixture was subjected to phase separation, and the toluene layer was washed twice with 10 g of water and then concentrated to give 5.9 g of an oil containing 5.7 g (96% yield) of ethyl 2-oxo-4-phenylbutanoate. The analysis by gas chromatography revealed that the percent area free of the solvent was 96.4% for ethyl 2-oxo-4-phenylbutanoate and 0.07% for (2-bromoethyl)benzene, and was reduced to 3.6% in total for the other impurities.

Example 13

In accordance with Example 10 until the crude product of ethyl 2-oxo-4-phenylbutanoate was obtained, a toluene solution containing 30.1% by weight of ethyl 2-oxo-4-phenylbutanoate and 3.9% by weight of (2-bromoethyl) benzene was prepared. To 3.43 g (5.0 mmol) of the toluene solution were added 0.89 g (4.5 mmol) of 50% aqueous ammonium hydrogensulfite solution and 1.78 g of water, and the mixture was stirred at 5° C. for 6 hours. The reaction mixture was subjected to phase separation at the same temperature, and the water layer was washed with 2 ml of toluene and then freeze-dried to give 1.37 g of an ammonium hydrogensulfite adduct of ethyl 2-oxo-4-phenylbutanoate. The content of the ammonium hydrogensulfite adduct of ethyl 2-oxo-4-phenylbutanoate was 96.1% by weight (95% yield).

$^1$H-NMR of the ammonium hydrogensulfite adduct of ethyl 2-oxo-4-phenylbutanoate (270 MHz, DMSO-$d_6$): δ6 1.20 (t, 3H, J=7.1 Hz), 1.95–2.15 (m, 1H), 2.2–2.5 (m, 2H), 2.6–2.8 (m, 1H), 3.95–4.25 (m, 2H), 6.0–7.6 (br, 5H), 7.05–7.2 (m, 3H), 7.2–7.35 (m, 2H)

Example 14

A mixture of 205 g (1.11 mol) of 1-bromo-5-chloropentane, 121 g (0.93 mol) of ethyl 3-oxobutanoate, and 109 g of n-heptane was heated to 100° C, and after the addition of 72 g (0.52 mol) of potassium carbonate, was stirred at the same temperature for 22 hours. In the middle of the stirring, more potassium carbonate was added at 72 g (0.52 mol) on 2 and 8.4 hours later, respectively, and at 26 g (0.18 mol) on 18 hours later. The reaction mixture was cooled to room temperature, after which inorganic salts were filtered off and the filtered solid was washed with 148 g of n-heptane. The combined filtrates were concentrated under reduced pressure to give 230 g of the crude product of ethyl 7-chloro-2-(1-oxoethyl)heptanoate. In the crude product, 63.0% by weight (66% yield) of ethyl 7-chloro-2-(1-oxoethyl)heptanoate and 11.8% by weight of 1-bromo-5-chloropentane were contained. The crude product was used as such in the next step without purification.

Then, 230 g (0.62 mol) of the crude product of ethyl 7-chloro-2-(1-oxoethyl)heptanoate thus obtained was cooled to 5° C., to which 228 g (0.81 mol) of 44% nitrosylsulfuric acid/sulfuric acid solution was added dropwise over 6 hours, and the mixture was further stirred at the same temperature for 4 hours. In another flask, 113 g (1.39 mol) of 37% aqueous formalin solution and 291 g of toluene were placed and then cooled to 10° C., to which the above reaction solution was added dropwise at the same temperature over 2 hours, and the mixture was further stirred at the same temperature for 30 minutes. The reaction mixture was subjected to phase separation, and the oil layer was washed with 107 g of 5% aqueous sodium carbonate solution and then with 107 g of water to give 508 g of a toluene solution containing ethyl 7-chloro-2-oxoheptanoate. In the toluene solution, 18.1% by weight (72% yield) of ethyl 7-chloro-2-oxoheptanoate and 5.4% by weight of 1-bromo-5-chloropentane were contained. The analysis by gas chromatography revealed that the percent area free of the solvent was 55.1% for ethyl 7-chloro-2-oxoheptanoate and 13.8% for 1-bromo-5-chloropentane, and the other impurities were contained at 31.1% in total. This toluene solution was used as such in the next step without purification.

Then, 508 g (0.44 mol) of the toluene solution of ethyl 7-chloro-2-oxoheptanoate thus obtained was added dropwise to a mixture of 56.3 g (0.51 mol) of sodium hydrogensulfite and 225 g of water at 20–30° C. over 2 hours. The reaction mixture, after the addition of 305 g of toluene, was subjected to phase separation to give 365 g of the water layer containing a sodium hydrogensulfite adduct of ethyl 7-chloro-2-oxoheptanoate. The separated oil layer, after the further addition of 28.1 g (0.26 mol) of sodium hydrogensulfite and 113 g of water, was stirred at 22° C. for 1 hour and then subjected to phase separation to give 170 g of the water layer. The water layers were combined, and after the addition of 383 g of toluene, was heated to 50° C., to which 101 g (0.99 mol) of 36% hydrochloric acid was added dropwise at the same temperature over 3.3 hours, and the mixture was further stirred at the same temperature for 40 minutes. The reaction mixture was subjected to phase separation, and the toluene layer was washed with 70 g of water and then concentrated to give an oil containing 89.5 g (97% yield) of ethyl 7-chloro-2-oxoheptanoate. The analysis by gas chromatography revealed that the percent area free of the solvent was 85.9% for ethyl 7-chloro-2-oxoheptanoate and 0.25% for 1-bromo-5-chloropentane, and was reduced to 13.9% in total for the other impurities.

Example 15

First, 6.19 g of an oil containing 4.95 g (24 mmol) of ethyl 2-oxo-4-phenylbutanoate and 1.08 g of diethyl oxalate was dissolved in 19.6 g of toluene, and the solution was added dropwise to a mixture of 3.15 g (29 mmol) of sodium hydrogensulfite and 12.6 g of water at 50° C. over 1 hour, and the mixture was further stirred for 2 hours. The reaction mixture was subjected to phase separation to give the water layer containing a sodium hydrogensulfite adduct of ethyl 2-oxo-4-phenylbutanoate. The separated oil layer, after the further addition of 1.58 g (14 mmol) of sodium hydrogensulfite and 3.7 g of water, was stirred at 50° C. for 1 hour and then subjected to phase separation. The water layer was washed once with 25 ml of toluene, and after the addition of 24 g of toluene, was heated to 50° C., to which 18.0 g (28 mmol) of 15% sulfuric acid was added dropwise at the same temperature over 1 hour, and the mixture was further stirred at the same temperature of 1 hour. The reaction mixture was subjected to phase separation, and the toluene layer was washed with 10 ml of water and then concentrated to give 4.15 g of an oil containing 4.05 g of ethyl 2-oxo-4-phenylbutanoate. The analysis by gas chromatography revealed the percent area free of the solvent was 97.9% for ethyl 2-oxo-4-phenylbutanoate and 0.04% for diethyl oxalate.

Example 16

A mixture of 5.00 g (30 mmol) of methyl 2-oxo-2-phenylethanoate and 2.00 g of methyl 2-hydroxy-2-phenylethanoate dissolved in 8.0 g of toluene was analyzed by gas chromatography, revealing that the percent area free of the solvent was 70.4% for methyl 2-oxo-2-phenylethanoate and 29.1% for methyl 2-hydroxy-2-phenylethanoate. The mixture was added dropwise to a mixture of 7.24 g (37 mmol) of 50% ammonium hydrogensulfite and 7.24 g of water at 5° C. over 0.5 hour, and the mixture was further stirred at the same temperature for 2 hours. The reaction mixture was subjected to phase separation, and the water layer was washed once with 7.5 g of toluene to give 19.8 g of the water layer containing 7.12 g (89% yield) of an ammonium hydrogensulfite adduct of methyl 2-oxo-2-phenylethanoate. The water layer, after the addition of 10 ml of toluene, was heated to 50° C., to which 3.66 g (37 mmol) of 98% sulfuric acid was added dropwise at the same temperature over 0.5 hour, and the mixture was further stirred at the same temperature for 1.5 hours. The reaction mixture was subjected to phase separation, and the toluene layer was washed twice with 10 ml of water and then concentrated to give 4.37 g of an oil containing 4.01 g (90% yield) of methyl 2-oxo-2-phenylethanoate. The analysis by gas chromatography revealed that the percent area of each component was 91.9% for methyl 2-oxo-2-phenylethanoate and 8.1% for methyl 2-hydroxy-2-phenylethanoate.

Industrial Applicability

The method of the present invention makes it possible to achieve the simple and easy purification of pyruvic acid compounds (I) or (VIII) by simple and easy procedures without using purification techniques such as distillation or column chromatography, and is useful as their production process on an industrial scale.

What is claimed is:
1. A method for purifying a crude pyruvic acid compound of general formula (I):

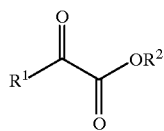

(I)

wherein $R^1$ is an optionally substituted lower alkyl group, an optionally substituted lower alkenyl group, an optionally substituted lower alkynyl group, an optionally substituted cycloalkyl group, an optionally substituted aryl group, or an optionally substituted heterocyclic group, and $R^2$ is a lower alkyl group, which method is characterized in that the crude pyruvic acid optionally substituted lower alkenyl group, an optionally compound of general formula (I) is reacted in water with a bisulfite of general formula (II):

MHSO$_3$ (II)

wherein M is NH$_4$ or an alkali metal, to give an aqueous solution of a bisulfite adduct of the pyruvic acid compound; said aqueous solution is isolated by phase separation optionally using a hydrophobic solvent and the adduct in the separated aqueous solution of the adduct is then contacted with an acid to decompose the adduct.

2. A process for producing a high-purity pyruvic acid compound of general formula (VIII):

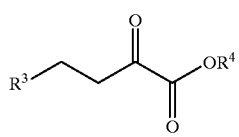

(VIII)

wherein $R^3$ is an optionally substituted lower alkyl group or an optionally substituted aryl group, and $R^4$ is an optionally substituted lower alkyl group, which process is characterized in that an alkane compound of general formula (III):

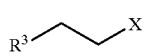

(III)

wherein $R^3$ is as defined above, and X is a halogen atom or a sulfonyloxy group, is reacted with a β-keto ester compound of general formula (IV):

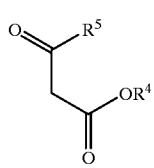

(IV)

wherein $R^4$ is as defined above, and $R^5$ is an optionally substituted lower alkyl group or an optionally substituted lower alkoxy group in the presence of a base, to give a diketo compound of general formula (V):

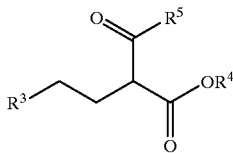
(V)

wherein $R^3$, $R^4$, and $R^5$ are as defined above; and the diketo compound of the general formula (VI):

Y—N=O    (VI)

wherein Y is a hydroxyl group, a lower alkoxy group, a halogen atom, or a —OSO$_3$H group, to give an α-oximino ester compound of general formula (VII):

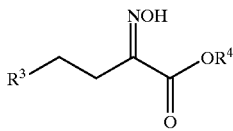
(VII)

wherein $R^3$ and $R^4$ are as defined above; and the α-oximino ester compound of general formula (VII) is then reacted with an aldehyde compound in the presence of an acid to give a crude product of the pyruvic acid compound of general formula (VIII):

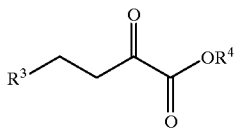
(VIII)

wherein $R^3$ and $R^4$ are as defined above; and the crude product is then reacted in water with a bisulfite of general formula (II):

MHSO$_3$    (II)

wherein M is NH$_4$ or an alkali metal, to give an aqueous solution of bisulfite adduct of the pyruvic acid compound; said aqueous solution is isolated by phase separation optionally using a hydrophobic solvent and the adduct in the separated aqueous solution of the adduct is then contacted with an acid to decompose the adduct.

3. The method according to claim 1, which is characterized in that the reaction temperature is set at 0° C. to 80° C. in the step of reacting the pyruvic acid compound of general formula (I) with the bisulfite of general formula (II) to give the bisulfite adduct of the pyruvic acid compound.

4. The process according to claim 2, which is characterized in that potassium carbonate is used as a base in the step of reacting the alkane compound of general formula (III) with the β-keto ester compound of general formula (IV) to give the diketo compound of general formula (V).

5. The process according to claim 4, which is characterized in that the reaction is carried out in the presence of water at an amount 0.005 to 0.08 time by weight, relative to the potassium carbonate, in the step of reacting the alkane compound of general formula (III) with the β-keto ester compound of general formula (IV) to give the diketo compound of general formula (V).

* * * * *